US005721115A

United States Patent [19]

Krivan et al.

[11] Patent Number: 5,721,115

[45] Date of Patent: Feb. 24, 1998

[54] DNA ENCODING A NOVEL *HAEMOPHILUS INFLUENZAE* PROTEIN

[75] Inventors: Howard C. Krivan, Bethesda; James E. Samuel, Germantown, both of Md.

[73] Assignee: Antex Biologics, Inc., Gaithersburg, Md.

[21] Appl. No.: 480,993

[22] Filed: Jun. 7, 1995

Related U.S. Application Data

[60] Division of Ser. No. 903,079, Jun. 22, 1992, which is a continuation-in-part of Ser. No. 810,966, Dec. 20, 1991, abandoned, which is a continuation-in-part of Ser. No. 631,698, Dec. 21, 1990, abandoned.

[51] Int. Cl.$^6$ .......................... C12P 21/06; C12N 15/06; C07H 21/02

[52] U.S. Cl. .................... 435/69.1; 435/69.3; 435/320.1; 424/200.1; 424/256.1; 536/23.1; 536/23.7; 530/350

[58] Field of Search ................................ 435/69.1, 69.3, 435/320.1; 424/256.1, 200.1; 536/23.1, 23.7; 530/350

[56] References Cited

U.S. PATENT DOCUMENTS

| | | | |
|---|---|---|---|
| 4,451,466 | 5/1984 | Vandevelde et al. . | |
| 4,455,296 | 6/1984 | Hansen et al. . | |
| 4,673,574 | 6/1987 | Anderson . | |
| 4,762,713 | 8/1988 | Anderson . | |
| 4,795,803 | 1/1989 | Lindberg et al. . | |
| 4,808,700 | 2/1989 | Anderson et al. . | |
| 4,830,852 | 5/1989 | Marburg et al. . | |
| 4,859,769 | 8/1989 | Karlsson et al. . | |
| 5,013,664 | 5/1991 | Brodeur et al. . | |
| 5,098,997 | 3/1992 | Anilionis et al. | 530/350 |
| 5,108,744 | 4/1992 | Deich et al. . | |
| 5,110,908 | 5/1992 | Deich et al. . | |

FOREIGN PATENT DOCUMENTS

| | | |
|---|---|---|
| 0098581 | 1/1984 | European Pat. Off. . |
| 0245045 | 11/1987 | European Pat. Off. . |
| 0276516 | 8/1988 | European Pat. Off. . |
| 0281673 | 9/1988 | European Pat. Off. . |
| 0320942 | 6/1989 | European Pat. Off. . |
| 0338265 | 10/1989 | European Pat. Off. . |
| 0378929 | 7/1990 | European Pat. Off. . |
| WO 86/06635 | 11/1986 | WIPO . |
| WO 89/12460 | 12/1989 | WIPO . |
| WO 90/02557 | 3/1990 | WIPO . |
| WO 91/06652 | 5/1991 | WIPO . |

OTHER PUBLICATIONS

Anderson et al., 1988, Vaccine 6:188–191.

Audibert et al., 1993, "Adjuvants: current status, clinical perspectives and future prospects", Immun. Today 14:281–284.

Barenkamp et al., 1981, "Subtyping Isolates of *Haemophilus* Type b by Outer–Membrane Protein Profiles", J. of Infect. Diseases 143:668–675.

Boons et al., 1991, "Preparation of a Well–Defined Sugar–Peptide Conjugate: a Possible Approach to a Synthetic Vaccine against *Neisseria meningitidis*", Bioorg. & Med. Chem. Lett. 1:303–308.

Chan et al., 1988, "A new approach to the synthesis of a dimeric fragment of the capsular polysaccharide of *Haemophilus influenzae* type b", Tetrahedron Letters 29:4049–4052.

Chan et al., 1990, "Synthesis of oligomers of the capsular polysaccharide of the *Haemophilus influenzae* Type b Bacteria", Tetrahedron 46:151–162.

Elie et al., 1989, "Synthesis of Fragments of the Capsular Polysaccharide of *Haemophilus influenzae* Type b Part III$^{1-3}$, A Solid–phase Synthesis of a Spacer–containing Ribosylribitol Phosphate Hexamer," Recueil des Travaux Chimiques des pays–Bas 108:219–223.

Erwin et al., 1988, "Human Antibody Response to Outer Membrane Proteins and Fimbriae of *Haemophilus influenzae* type b", Can. J. Microbiol. 34:723–729.

Forney et al., 1991, "Comparison and Analysis of the Nucleotide Sequencer of Pilin Genes from *Haemophilus influenzae* Type b Strains Eagan and M43", Infect. & Immun. 59:1991–1996.

Gonzales et al., 1987, "Cloning and Expression in *Escherichia coli* of the $_{13}$ Encoding the Heat–Modifiable Major Outer Membrane Protein of *Haemophilus influenzae* Type b", infect. & Immun. 55:2993–3000.

Green et al., 1993, "Evaluation of Mixtures of Purified *Haemophilus influenzae* Outer Membrane Proteins in Protection against Challenge with Nontypeable *H. influenzae* in the Chinchilla Otitis Media Model", Infect. & Immun. 61:1950–1957.

Griffiths, 19$_{13}$, Bacterial Vaccines pp. 861–867.

Gulig et al., 1983, Infect. & Immun. 42:516–524.

Hanson et al., 1989, Infect. & Immun. 57:1639–1646.

Honberg, 1985, "Subtyping of Danish *Haemophilus influenzae* Type B by Their 45000 and 46000 Molecular Weight Proteins", Acta Path. Microbio. Immun. Scand. 93:175–179.

Hoogerhout et al., 1987, "Synthesis of fragments of the capsular polysaccharide of the *Haemophilus influenza* Type B, comprising two or three repeating units", Tetrahedron Letters 28:1553–1556.

Johnson et al., 1993, Infect. & Immun. 61:1531–1537.

Juhn et al., 1991, "The Significance of Experimental Animal Studies in Otitis Media", Otitis Media: The Pathogenesis Approach 24:813–827.

(List continued on next page.)

*Primary Examiner*—James C. Housel
*Assistant Examiner*—Jennifer Shaver
*Attorney, Agent, or Firm*—Pennie & Edmonds

[57] ABSTRACT

Disclosed herein are an immunogenic *Haemophilus influenzae* outer membrane protein of 49 kDa as well as a mature outer membrane protein of 47 kDa protein, DNA and vector useful for producing the outer membrane protein, host cell containing said DNA, and a method for producing the outer membrane protein. Also disclosed are methods for producing these materials which can be beneficially used in the production of vaccines against *H. influenzae*.

13 Claims, 10 Drawing Sheets

OTHER PUBLICATIONS

Krivan et al., 1988, "Many Pulmonary Pathogenic Bacteria Bind Specifically to the Carbohydrate Sequence GalNAcβ, 1–4Gal Found in Some Glycolipids", Proceedings of the Natl. Academy of Sciences (USA) 85:6157–6161.

Langermann et al., 1990, "Molecular Analysis of the *Haemophilus influenzae* Type b Pilin Gene", Molecular Microbio. pp. 221–230.

Leith et al., 1984, "Purification of a *Mycoplasma pneumoniae* adhesin by Monoclonal Antibody Affinity Chromatography", J. of Bacteriol. 157:678–680.

Loeb et al., 1981, J. of Bacteriol. 145:596–604.

Loeb et al., 1987, Infect. & Immun. 55:2977–2983.

Moxon et al., 1988, Vaccine 6:113–115.

Munson et al., 1983, Clin. Invest. 72:677–684.

Munson et al., 1985, "Purification and Partial Characterization of Outer Membrane Proteins P5 and P6 from *Haemophilus influenzae* Type b", Infect. & Immun. 49:544–549.

Munson et al., 1988, "Purification, Cloning, and Sequence of Outer Membrane Protein P1 of *Haemophilus influenzae* Type b", Infect. & Immun. 56:2235–2242.

Munson et al., 1989, Infect. & Immun. 57:1002–1004.

Munson et al., 1989, Infect. & Immun. 57:3300–3305.

Raun et al., 1990, "Protein D of *Haemophilus influenzae*", J. of Immun. 145:3379–3384.

Robertson et al., $19_{13}$, "Monoclonal Antibodies Directed Against a Cell Surface–Exposed Outer Membrane Protein of *Haemophilus influenzae* Type B".

St. Geme, 1993, "Nontypeable *Haemophilus influenzae* Disease: Epidemiology, Pathogenesis, and Prospects for Prevention", Infectious Agents & Disease 2:1–16.

Vachon et al., 1985, "Transmembrane Permeability Channels Across the Outer Membrane of *Haemophilus influenzae* Type B", J. of Bacteriol. 162:918–924.

van Aldhen et al., 1983, "Characteristics of Major Outer Membrane Proteins of *Haemophilus influenzae*", J. of Bact. 155:878–885.

van Hahm et al., 1989, "Cloning and Expression in *Escherichia coli* of *Haemophiluis influenzae* Fimbrial Genes Establishes Adherence of Oropharyngeal Epithelial Cells", EMBO Journal 8:3535–3540.

Wang et al., 1988, "Synthesis of fragments of the capsular polysaccharide of *Haemophilus influenzae* Type B", Tetrahedron Letters 29:1525–1528.

Weinstein et al., 1992, "Cloning and Characterization of an *Haemophilus influenzae* Type b Adhesin", Abstracts of the 92nd Gen. Meeting of the ASM p. 136, Abstr. D–243.

Young et al., 1983, "Efficient Isolation of Genes by Using Antibody Probes", Proc. Natl. Acad. Sci. USA 80:1194–1198.

Barenkamp & Leininger, 1992, "Cloning, expression, and DNA sequence analysis of genes encoding nontypeable *Haemophilus influenzae* high–molecular–weight surface––exposed proteins related to filamentous hemagglutinin of *Bordetella pertussis*", *Infect. Immun.* 60:1302–1313.

Chanyangam et al., 1991, "Contribution of a 20–kilodalton membrane protein to the virulence of *Haemophilus influenzae*", *Infect. Immun.* 59:600–608.

Deich et al., 1988, "Cloning of genes encoding a 15,000–dalton peptidoglycan–associated outer membrane lipoprotein and an antigenically related 15,000–dalton protein from *Haemophilus influenzae*", *J. Bact.* 170:489–498.

Coulton et al., 1992, "Recombinant porin of *Haemophilius influenzae* type b", *J. Infect. Dis.* 165:Suppl. 1:S188–S191.

Green et al., 1991, "The e(P4) outer membrane protein of *Haemophilus influenzae:* Biologic activity of anti–e serum and cloning and sequencing of the structural gene", *Infect. Immun.* 59:3191–3198.

Hansen et al., 1988, "Cloning of the gene encoding the major outer membrane protein of *Haemophilus influenzae* type b", *Infect. Immun.* 56:2709–2716.

Hansen et al., 1989, "Primary structure of the porin protein of *Haemophilus influenzae* type b determined by nucleotide sequence analysis", *Infect. Immun.* 57:1100–1107.

Holmans et al., 1985, "Cloning and surface expression in *Escherichia coli* of a structural gene encoding a surface protein of *Haemorphilus influenzae* type b", *Infect. Immun.* 50:236–242.

Kimura et al., 1985, "A minor high–molecular–weight outer membrane protein of *Haemophilus influenzae* type b is a protective antigen", *Infect. Immun.* 47:253–259.

Loeb, 1987, "Protection of infant rats from *Haemophilus influenzae* type b infection by antiserum to purified outer membrane protein a", *Infect. Immun.* 55:2612–2618.

Munson et al., 1989, "Molecular cloning, expression, and primary sequence of outer membrane protein P2 of *Haemophilus influenzae* type b", *Infect. Immun.* 57:88–94.

Munson et al., 1993, "Molecular cloning and sequence of the gene for outer membrane protein P5 of *Haemophilus influenzae*", *Infect. Immun.* 61:4017–4020.

Murphy & Bartos, 1988, "Purification and analysis with monoclonal antibodies of P2, the major outer membrane protein of nontypeable *Haemophilus influenzae*", *Infect. Immun.* 56:1084–1089.

Nelson et al., 1988, "Cloning and sequencing of *Haemophilus influenzae* outer membrane protein P6", *Infect. Immun.* 56:128–134.

Thomas et al., 1990, "Expression in *Escherichia coli* of a high–molecular–weight protective surface antigen found in nontypeable and type b *Haemophilus influenzae*", *Infect. Immun.* 58:1909–1913.

Vachon et al., 1988, "Outer membrane porin protein of *Haemophilus influenzae* type b: Pore size and subunit structure", *Can. J. Microbiol.* 34:134–140.

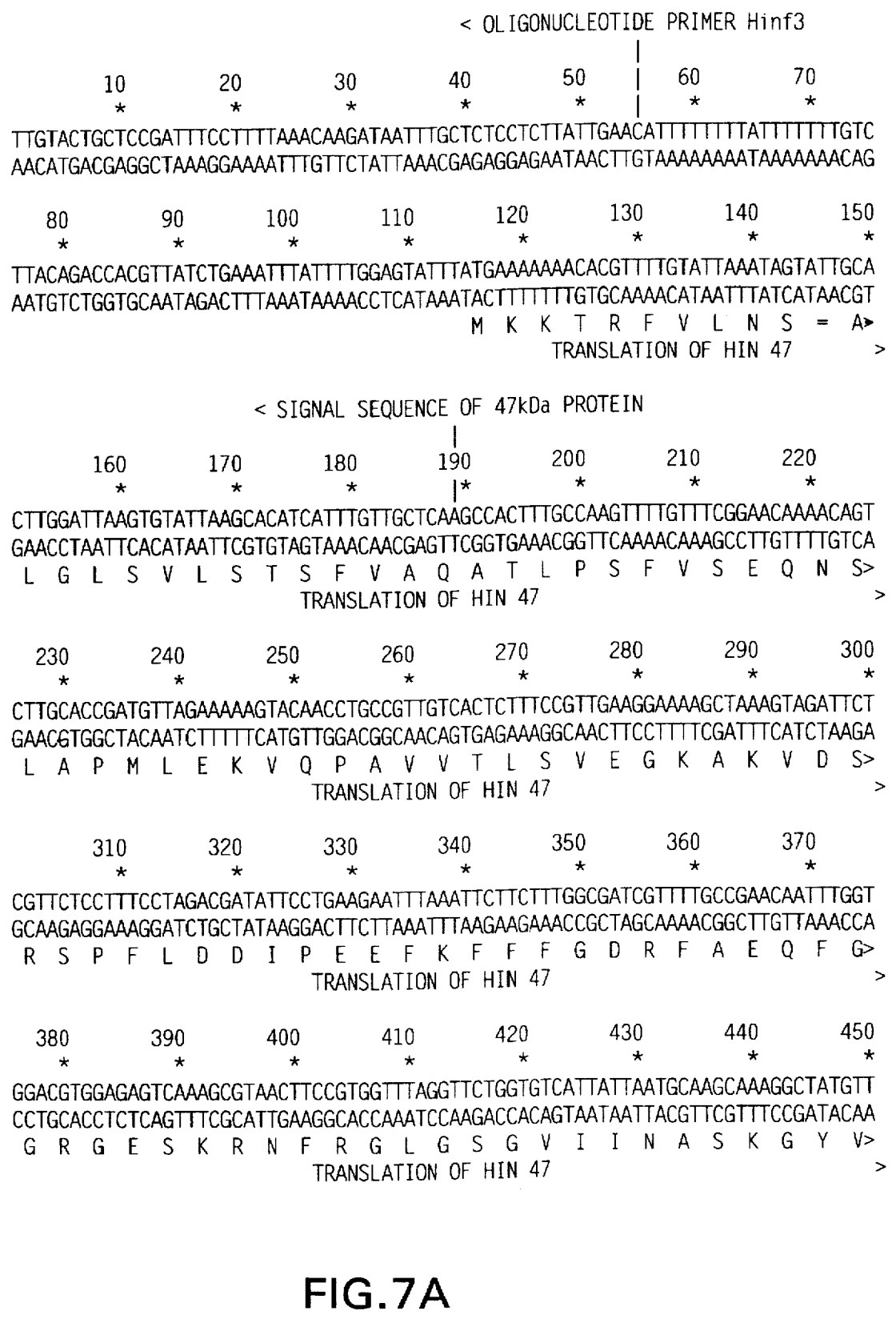

< OLIGONUCLEOTIDE PRIMER Hinf3

10 20 30 40 50 | 60 70

TTGTACTGCTCCGATTTCCTTTTAAACAAGATAATTTGCTCTCCTCTTATTGAACATTTTTTTTATTTTTTTTGTC
AACATGACGAGGCTAAAGGAAAATTTGTTCTATTAAACGAGAGGAGAATAACTTGTAAAAAAAATAAAAAAAACAG 80 90 100 110 120 130 140 150

TTACAGACCACGTTATCTGAAATTTATTTTGGAGTATTTATGAAAAAAACACGTTTTGTATTAAATAGTATTGCA
AATGTCTGGTGCAATAGACTTTAAATAAAACCTCATAAATACTTTTTTTGTGCAAAACATAATTTATCATAACGT
M K K T R F V L N S = A>
TRANSLATION OF HIN 47 >

< SIGNAL SEQUENCE OF 47kDa PROTEIN 160 170 180 190 | 200 210 220

CTTGGATTAAGTGTATTAAGCACATCATTTGTTGCTCAAGCCACTTTGCCAAGTTTTGTTTCGGAACAAAACAGT
GAACCTAATTCACATAATTCGTGTAGTAAACAACGAGTTCGGTGAAACGGTTCAAAACAAAGCCTTGTTTTGTCA
L G L S V L S T S F V A Q A T L P S F V S E Q N S>
TRANSLATION OF HIN 47 >

230 240 250 260 270 280 290 300

CTTGCACCGATGTTAGAAAAAGTACAACCTGCCGTTGTCACTCTTTCCGTTGAAGGAAAAGCTAAAGTAGATTCT
GAACGTGGCTACAATCTTTTTCATGTTGGACGGCAACAGTGAGAAAGGCAACTTCCTTTTCGATTTCATCTAAGA
L A P M L E K V Q P A V V T L S V E G K A K V D S>
TRANSLATION OF HIN 47 >

310 320 330 340 350 360 370

CGTTCTCCTTTCCTAGACGATATTCCTGAAGAATTTAAATTCTTCTTTGGCGATCGTTTTGCCGAACAATTTGGT
GCAAGAGGAAAGGATCTGCTATAAGGACTTCTTAAATTTAAGAAGAAACCGCTAGCAAAACGGCTTGTTAAACCA
R S P F L D D I P E E F K F F F G D R F A E Q F G>
TRANSLATION OF HIN 47 >

380 390 400 410 420 430 440 450

GGACGTGGAGAGTCAAAGCGTAACTTCCGTGGTTTAGGTTCTGGTGTCATTATTAATGCAAGCAAAGGCTATGTT
CCTGCACCTCTCAGTTTCGCATTGAAGGCACCAAATCCAAGACCACAGTAATAATTACGTTCGTTTCCGATACAA
G R G E S K R N F R G L G S G V I I N A S K G Y V>
TRANSLATION OF HIN 47 >

FIG.7A

```
        460       470       480       490       500       510       520
         *         *         *         *         *         *         *
TTAACCAATAATCATGTTATTGATGGAGCTGATAAAATTACCGTGCAATTACAAGATGGGCGTGAATTTAAAGCA
AATTGGTTATTAGTACAATAACTACCTCGACTATTTTAATGGCACGTTAATGTTCTACCCGCACTTAAATTTCGT
 L  T  N  N  H  V  I  D  G  A  D  K  I  T  V  Q  L  Q  D  G  R  E  F  K  A>
                         TRANSLATION OF HIN 47                             >

   530       540       550       560       570       580       590       600
    *         *         *         *         *         *         *         *
AAATTAGTGGGTAAAGATGAACAATCAGATATTGCATTAGTACAGCTTGAAAAACCAAGTAATTTAACAGAAATC
TTTAATCACCCATTTCTACTTGTTAGTCTATAACGTAATCATGTCGAACTTTTTGGTTCATTAAATTGTCTTTAG-
 K  L  V  G  K  D  E  Q  S  D  I  A  L  V  Q  L  E  K  P  S  N  L  T  E  I>
                         TRANSLATION OF HIN 47                             >

        610       620       630       640       650       660       670
         *         *         *         *         *         *         *
AAATTTGCTGATTCCGACAAATTACGCGTAGGCGATTTCACTGTTGCAATCGGTAATCCATTTGGTTTAGGTCAA
TTTAAACGACTAAGGCTGTTTAATGCGCATCCGCTAAAGTGACAACGTTAGCCATTAGGTAAACCAAATCCAGTT
 K  F  A  D  S  D  K  L  R  V  G  D  F  T  V  A  I  G  N  P  F  G  L  G  Q>
                         TRANSLATION OF HIN 47                             >

   680       690       700       710       720       730       740       750
    *         *         *         *         *         *         *         *
ACTGTGACATCAGGTATTGTTTCTGCATTGGGTCGTTCAACAGGTTCTGACAGTGGCACTTATGAAAACTATATT
TGACACTGTAGTCCATAACAAAGACGTAACCCAGCAAGTTGTCCAAGACTGTCACCGTGAATACTTTTGATATAA
 T  V- T  S  G  I  V  S  A  L  G  R  S  T  G  S  D  S  G  T  Y  E  N  Y  I>
                         TRANSLATION OF HIN 47                             >

        760       770       780       790       800       810       820
         *         *         *         *         *         *         *
CAAACCGATGCAGCAGTAAACCGCGGTAATTCGGGTGGTGCATTAGTCAATCTAAATGGCGAACTTATTGGAATT
GTTTGGCTACGTCGTCATTTGGCGCCATTAAGCCCACCACGTAATCAGTTAGATTTACCGCTTGAATAACCTTAA
 Q  T  D  A  A  V  N  R  G  N  S  G  G  A  L  V  N  L  N  G  E  L  I  G  I>
                         TRANSLATION OF HIN 47                             >

   830       840       850       860       870       880       890       900
    *         *         *         *         *         *         *         *
AATACCGCAATTATTTCTCCAAGCGGTGGCAATGCAGGAATTGCCTTTGCGATTCCAAGTAATCAAGCAAGCAAT
TTATGGCGTTAATAAAGAGGTTCGCCACCGTTACGTCCTTAACGGAAACGCTAAGGTTCATTAGTTCGTTCGTTA
 N  T  A  I  I  S  P  S  G  G  N  A  G  I  A  F  A  I  P  S  N  Q  A  S  N>
                         TRANSLATION OF HIN 47                             >
```

FIG.7B

```
      910       920       930       940       950       960       970
        *         *         *         *         *         *         *
TTAGTGCAACAAATTTTAGAATTTGGTCAAGTGCGTCGCGGATTGCTTGGTATTAAAGGGGGCGAACTCAATGCT
AATCACGTTGTTTAAAATCTTAAACCAGTTCACGCAGCGCCTAACGAACCATAATTTCCCCCGCTTGAGTTACGA
 L  V  Q  Q  I  L  E  F  G  Q  V  R  R  G  L  L  G  I  K  G  G  E  L  N  A>
                        TRANSLATION OF HIN 47                               >

    980       990      1000      1010      1020      1030      1040      1050
      *         *         *         *         *         *         *         *
GATTTAGCCAAAGCCTTTAATGTAAGCGCGCAACAAGGTGCATTTGTAAGTGAAGTTTTACCGAAATCTGCTGCT
CTAAATCGGTTTCGGAAATTACATTCGCGCGTTGTTCCACGTAAACATTCACTTCAAAATGGCTTTAGACGACGA
 D  L  A  K  A  F  N  V  S  A  Q  Q  G  A  F  V  S  E  V  L  P  K  S  A  A>
                        TRANSLATION OF HIN 47                               >

     1060      1070      1080      1090      1100      1110      1120
        *         *         *         *         *         *         *
GAAAAAGCAGGACTTAAAGCGGGCGATATTATCACGGCGATGAACGGTCAAAAAATCTCAAGTTTCGCTGAAATT
CTTTTTCGTCCTGAATTTCGCCCGCTATAATAGTGCCGCTACTTGCCAGTTTTTTAGAGTTCAAAGCGACTTTAA
 E  K  A  G  L  K  A  G  D  I  I  T  A  M  N  G  Q  K  I  S  S  F  A  E  I>
                        TRANSLATION OF HIN 47                               >

   1130      1140      1150      1160      1170      1180      1190      1200
      *         *         *         *         *         *         *         *
CGTGCAAAAATCGCAACCACTGGTGCAGGCAAAGAGATTAGCTTGACTTACTTACGTGATGGCAAATCCCACGAC
GCACGTTTTTAGCGTTGGTGACCACGTCCGTTTCTCTAATCGAACTGAATGAATGCACTACCGTTTAGGGTGCTG
 R  A  K  I  A  T  T  G  A  G  K  E  I  S  L  T  Y  L  R  D  G  K  S  H  D>
                        TRANSLATION OF HIN 47                               >

     1210      1220      1230      1240      1250      1260      1270
        *         *         *         *         *         *         *
GTTAAAATGAAATTACAAGCGGATGATGGTAGCCAACTTTCCTCAAAAACTGAGTTGCCTGCATTAGATGGCGCA
CAATTTTACTTTAATGTTCGCCTACTACCATCGGTTGAAAGGAGTTTTTGACTCAACGGACGTAATCTACCGCGT
 V  K  M  K  L  Q  A  D  D  G  S  Q  L  S  S  K  T  E  L  P  A  L  D  G  A>
                        TRANSLATION OF HIN 47                               >

   1280      1290      1300      1310      1320      1330      1340      1350
      *         *         *         *         *         *         *         *
ACATTGAAAGACTACGATGCTAAAGGCGTTAAAGGAATTGAAATCACAAAAATTCAACCTAATTCGCTGGCTGCA
TGTAACTTTCTGATGCTACGATTTCCGCAATTTCCTTAACTTTAGTGTTTTTAAGTTGGATTAAGCGACCGACGT
 T  L  K  D  Y  D  A  K  G  V  K  G  I  E  I  T  K  I  Q  P  N  S  L  A  A>
                        TRANSLATION OF HIN 47                               >

     1360      1370      1380      1390      1400      1410      1420
        *         *         *         *         *         *         *
CAACGTGGTTTAAAATCGGGCGATATTATTATTGGTATTAATCGTCAAATGATCGAAAACATTCGTGAATTAAAT
GTTGCACCAAATTTTAGCCCGCTATAATAATAACCATAATTAGCAGTTTACTAGCTTTTGTAAGCACTTAATTTA
 Q  R  G  L  K  S  G  D  I  I  I  G  I  N  R  Q  M  I  E  N  I  R  E  L  N>
                        TRANSLATION OF HIN 47                               >
```

FIG.7C

```
1430      1440      1450      1460      1470      1480      1490      1500
   *         *         *         *         *         *         *         *
AAAGTGCTTGAAACTGAACCGTCAGCAGTTGCACTTAATATTTTACGAGGTGACAGTAATTTCTATTTATTAGTG
TTTCACGAACTTTGACTTGGCAGTCGTCAACGTGAATTATAAAATGCTCCACTGTCATTAAAGATAAATAATCAC
 K  V  L  E  T  E  P  S  A  V  A  L  N  I  L  R  G  D  S  N  F  Y  L  L  V>
                           TRANSLATION OF HIN 47                           >

     1510      1520      1530      1540      1550      1560      1570
        *         *         *         *         *         *         *
CAATAATCTGCTTGATATATTTAAGAAAAAAGTCCGATCACAATGATCGGCTTCTTTTTATGCAGCAATCGTTCT
GTTATTAGACGAACTATATAAATTCTTTTTTCAGGCTAGTGTTACTAGCCGAAGAAAAATACGTCGTTAGCAAGA
 Q>
  >

            <OLIGONUCLEOTIDE PRIMER Hinf4
                          |
 1580      1590      1600 |  1610
    *         *         * |     *
TAACAAATCCACCACAAATTCTAACCGCACTTTGTT
ATTGTTTAGGTGGTGTTTAAGATTGGCGTGAAACAA
```

FIG.7D

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1611 base pairs
( B ) TYPE: nucleic acid
( C ) STRANDEDNESS: double
( D ) TOPOLOGY: unknown ( i i ) MOLECULE TYPE: DNA ( x i ) SEQUENCE DESCRIPTION: SEQ ID NO:1:

TTGTACTGCT CCGATTTCCT TTTAAACAAG ATAATTTGCT CTCCTCTTAT TGAACATTTT 60

TTTTATTTTT TTGTCTTACA GACCACGTTA TCTGAAATTT ATTTTGGAGT ATTTATGAAA 120

AAAACACGTT TTGTATTAAA TAGTATTGCA CTTGGATTAA GTGTATTAAG CACATCATTT 180

GTTGCTCAAG CCACTTTGCC AAGTTTTGTT TCGGAACAAA ACAGTCTTGC ACCGATGTTA 240

GAAAAAGTAC AACCTGCCGT TGTCACTCTT TCCGTTGAAG GAAAAGCTAA AGTAGATTCT 300

-continued

```
CGTTCTCCTT TCCTAGACGA TATTCCTGAA GAATTTAAAT TCTTCTTTGG CGATCGTTTT   360
GCCGAACAAT TTGGTGGACG TGGAGAGTCA AAGCGTAACT TCCGTGGTTT AGGTTCTGGT   420
GTCATTATTA ATGCAAGCAA AGGCTATGTT TTAACCAATA ATCATGTTAT TGATGGAGCT   480
GATAAAATTA CCGTGCAATT ACAAGATGGG CGTGAATTTA AAGCAAAATT AGTGGGTAAA   540
GATGAACAAT CAGATATTGC ATTAGTACAG CTTGAAAAAC CAAGTAATTT AACAGAAATC   600
AAATTTGCTG ATTCCGACAA ATTACGCGTA GGCGATTTCA CTGTTGCAAT CGGTAATCCA   660
TTTGGTTTAG GTCAAACTGT GACATCAGGT ATTGTTTCTG CATTGGGTCG TTCAACAGGT   720
TCTGACAGTG GCACTTATGA AAACTATATT CAAACCGATG CAGCAGTAAA CCGCGGTAAT   780
TCGGGTGGTG CATTAGTCAA TCTAAATGGC GAACTTATTG GAATTAATAC CGCAATTATT   840
TCTCCAAGCG GTGGCAATGC AGGAATTGCC TTTGCGATTC CAAGTAATCA AGCAAGCAAT   900
TTAGTGCAAC AAATTTTAGA ATTTGGTCAA GTGCGTCGCG GATTGCTTGG TATTAAAGGG   960
GGCGAACTCA ATGCTGATTT AGCCAAAGCC TTTAATGTAA GCGCGCAACA AGGTGCATTT  1020
GTAAGTGAAG TTTTACCGAA ATCTGCTGCT GAAAAAGCAG GACTTAAAGC GGGCGATATT  1080
ATCACGGCGA TGAACGGTCA AAAAATCTCA AGTTTCGCTG AAATTCGTGC AAAAATCGCA  1140
ACCACTGGTG CAGGCAAAGA GATTAGCTTG ACTTACTTAC GTGATGGCAA ATCCCACGAC  1200
GTTAAAATGA AATTACAAGC GGATGATGGT AGCCAACTTT CCTCAAAAAC TGAGTTGCCT  1260
GCATTAGATG GCGCAACATT GAAAGACTAC GATGCTAAAG GCGTTAAAGG AATTGAAATC  1320
ACAAAAATTC AACCTAATTC GCTGGCTGCA CAACGTGGTT TAAAATCGGG CGATATTATT  1380
ATTGGTATTA ATCGTCAAAT GATCGAAAAC ATTCGTGAAT TAAATAAAGT GCTTGAAACT  1440
GAACCGTCAG CAGTTGCACT TAATATTTTA CGAGGTGACA GTAATTTCTA TTTATTAGTG  1500
CAATAATCTG CTTGATATAT TTAAGAAAAA AGTCCGATCA CAATGATCGG CTTCTTTTTA  1560
TGCAGCAATC GTTCTTAACA AATCCACCAC AAATTCTAAC CGCACTTTGT T           1611
```

( 2 ) INFORMATION FOR SEQ ID NO:2:

( i ) SEQUENCE CHARACTERISTICS:
( A ) LENGTH: 463 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:2:

```
Met Lys Lys Thr Arg Phe Val Leu Asn Ser Ile Ala Leu Gly Leu Ser
1               5                   10                  15

Val Leu Ser Thr Ser Phe Val Ala Gln Ala Thr Leu Pro Ser Phe Val
            20                  25                  30

Ser Glu Gln Asn Ser Leu Ala Pro Met Leu Glu Lys Val Gln Pro Ala
        35                  40                  45

Val Val Thr Leu Ser Val Glu Gly Lys Ala Lys Val Asp Ser Arg Ser
    50                  55                  60

Pro Phe Leu Asp Asp Ile Pro Glu Glu Phe Lys Phe Phe Phe Gly Asp
65                  70                  75                  80

Arg Phe Ala Glu Gln Phe Gly Gly Arg Gly Glu Ser Lys Arg Asn Phe
                85                  90                  95

Arg Gly Leu Gly Ser Gly Val Ile Ile Asn Ala Ser Lys Gly Tyr Val
            100                 105                 110

Leu Thr Asn Asn His Val Ile Asp Gly Ala Asp Lys Ile Thr Val Gln
```

-continued

| | | | | | | | | | | | | | | | |
|---|---|---|---|---|---|---|---|---|---|---|---|---|---|---|---|
| | | 115 | | | | | 120 | | | | | 125 | | | |
| Leu | Gln | Asp | Gly | Arg | Glu | Phe | Lys | Ala | Lys | Leu | Val | Gly | Lys | Asp | Glu |
| | 130 | | | | | 135 | | | | | 140 | | | | |
| Gln | Ser | Asp | Ile | Ala | Leu | Val | Gln | Leu | Glu | Lys | Pro | Ser | Asn | Leu | Thr |
| 145 | | | | | 150 | | | | | 155 | | | | | 160 |
| Glu | Ile | Lys | Phe | Ala | Asp | Ser | Asp | Lys | Leu | Arg | Val | Gly | Asp | Phe | Thr |
| | | | | 165 | | | | | 170 | | | | | 175 | |
| Val | Ala | Ile | Gly | Asn | Pro | Phe | Gly | Leu | Gly | Gln | Thr | Val | Thr | Ser | Gly |
| | | | 180 | | | | | 185 | | | | | 190 | | |
| Ile | Val | Ser | Ala | Leu | Gly | Arg | Ser | Thr | Gly | Ser | Asp | Ser | Gly | Thr | Tyr |
| | | 195 | | | | | 200 | | | | | 205 | | | |
| Glu | Asn | Tyr | Ile | Gln | Thr | Asp | Ala | Ala | Val | Asn | Arg | Gly | Asn | Ser | Gly |
| | 210 | | | | | 215 | | | | | 220 | | | | |
| Gly | Ala | Leu | Val | Asn | Leu | Asn | Gly | Glu | Leu | Ile | Gly | Ile | Asn | Thr | Ala |
| 225 | | | | | 230 | | | | | 235 | | | | | 240 |
| Ile | Ile | Ser | Pro | Ser | Gly | Gly | Asn | Ala | Gly | Ile | Ala | Phe | Ala | Ile | Pro |
| | | | | 245 | | | | | 250 | | | | | 255 | |
| Ser | Asn | Gln | Ala | Ser | Asn | Leu | Val | Gln | Gln | Ile | Leu | Glu | Phe | Gly | Gln |
| | | | 260 | | | | | 265 | | | | | 270 | | |
| Val | Arg | Arg | Gly | Leu | Leu | Gly | Ile | Lys | Gly | Gly | Glu | Leu | Asn | Ala | Asp |
| | | 275 | | | | | 280 | | | | | 285 | | | |
| Leu | Ala | Lys | Ala | Phe | Asn | Val | Ser | Ala | Gln | Gln | Gly | Ala | Phe | Val | Ser |
| | 290 | | | | | 295 | | | | | 300 | | | | |
| Glu | Val | Leu | Pro | Lys | Ser | Ala | Ala | Glu | Lys | Ala | Gly | Leu | Lys | Ala | Gly |
| 305 | | | | | 310 | | | | | 315 | | | | | 320 |
| Asp | Ile | Ile | Thr | Ala | Met | Asn | Gly | Gln | Lys | Ile | Ser | Ser | Phe | Ala | Glu |
| | | | | 325 | | | | | 330 | | | | | 335 | |
| Ile | Arg | Ala | Lys | Ile | Ala | Thr | Thr | Gly | Ala | Gly | Lys | Glu | Ile | Ser | Leu |
| | | | 340 | | | | | 345 | | | | | 350 | | |
| Thr | Tyr | Leu | Arg | Asp | Gly | Lys | Ser | His | Asp | Val | Lys | Met | Lys | Leu | Gln |
| | | 355 | | | | | 360 | | | | | 365 | | | |
| Ala | Asp | Asp | Gly | Ser | Gln | Leu | Ser | Ser | Lys | Thr | Glu | Leu | Pro | Ala | Leu |
| | 370 | | | | | 375 | | | | | 380 | | | | |
| Asp | Gly | Ala | Thr | Leu | Lys | Asp | Tyr | Asp | Ala | Lys | Gly | Val | Lys | Gly | Ile |
| 385 | | | | | 390 | | | | | 395 | | | | | 400 |
| Glu | Ile | Thr | Lys | Ile | Gln | Pro | Asn | Ser | Leu | Ala | Ala | Gln | Arg | Gly | Leu |
| | | | | 405 | | | | | 410 | | | | | 415 | |
| Lys | Ser | Gly | Asp | Ile | Ile | Ile | Gly | Ile | Asn | Arg | Gln | Met | Ile | Glu | Asn |
| | | | 420 | | | | | 425 | | | | | 430 | | |
| Ile | Arg | Glu | Leu | Asn | Lys | Val | Leu | Glu | Thr | Glu | Pro | Ser | Ala | Val | Ala |
| | | 435 | | | | | 440 | | | | | 445 | | | |
| Leu | Asn | Ile | Leu | Arg | Gly | Asp | Ser | Asn | Phe | Tyr | Leu | Leu | Val | Gln | |
| | 450 | | | | | 455 | | | | | 460 | | | | |

DNA ENCODING A NOVEL *HAEMOPHILUS INFLUENZAE* PROTEIN

This is a divisional application of application Ser. No. 07/903,079, filed on Jun. 22, 1992, which is a continuation-in-part application of application Ser. No. 07/810,966 filed on Dec. 20, 1991, now abandoned, which is a continuation-in-part application of application Ser. No. 07/631,698, now abandoned, filed on Dec. 21, 1990, all of which are incorporated herein by reference in their entirety.

BACKGROUND OF THE INVENTION

This invention relates generally to vaccines against *Haemophilus influenzae.* In particular, it relates to a conjugate vaccine in which a synthetic oligosaccharide corresponding to a fragment of the polysaccharide capsule of *H. influenzae* type b has been coupled to an *H. influenzae* adhesin protein. The vaccine may be used against both invasive and non-invasive *H. influenzae* infection of humans, particularly very young infants, and other mammals.

*H. influenzae* (Hi) are divided into two groups, those strains that possess a polysaccharide capsule and those that do not. The encapsulated strains are typed by a serological reaction of a capsule with reference antisera. Types a–f have been identified. The non-encapsulated strains, which fail to react with any of the reference antisera, are known as non-typeable.

Hi are a significant health problem worldwide. The type b strain (Hib) is the most virulent of the Hi strains, causing meningitis, acute epiglottitis, and other life-threatening infections in children five years old and younger. The mortality rate from type b meningitis is about 5%, even with the best modern antibiotic treatments, and neurological sequelae are observed in as many as 25–35% of the survivors. In fact, bacterial meningitis caused by type b strains has been identified as the leading cause of acquired mental retardation in the United States. Thus, World Health Organization has made the development of an effective vaccine against Hib a priority.

Non-typeable Hi also cause various diseases, including pneumonia, bacteremia, meningitis, postpartum sepsis, bronchitis, sinusitis, conjunctivitis, and otitis media. The non-typeable Hi cause about 20–40% of all otitis media in children and young adults. Current therapy for chronic or repeated occurrences of otitis media generally involves antibiotic administration. Children may experience multiple infections because infection does not confer a lasting immunity.

A great deal of time, money, and effort has been spent trying to find a truly effective vaccine to *H. influenzae.* The overwhelming focus has been on developing a vaccine for Hib because of its serious threat to very young children. Unfortunately, the approved type b polysaccharide vaccines are not effective for children under 18 months of age, which is the group most threatened by Hib.

It has been known for many years that antibodies directed against the type b capsule will protect individuals against invasive Hib infection, including meningitis. In a randomized, double-blind clinical trial in Finland, a type b polysaccharide vaccine was found to be 90% effective in presenting disease in children immunized between 24 and 72 months of age. However, the vaccine conferred no protective immunity in children younger than 18 months and provided only limited immunity in children aged 18–23 months. Peltola, et al., *N. Engl. J. Med.,* 310: 1561–1566 (1984). The type b polysaccharide elicits a T-cell-independent immune response, which probably accounts for the low immunogenicity in young children.

Based on these data, three type b polysaccharide vaccines were licensed in the United States in 1985 and were recommended for use in children aged 24–60 months. These vaccines obviously have a major problem. They do not adequately protect children under 24 months of age, the group most susceptible to *H. influenzae* disease.

There are other problems relating to the fact that the polysaccharide is obtained from natural sources. Although purified, the polysaccharide fragments are of various lengths and, therefore, not as well characterized as desirable. This creates problems with respect to reproducibility and variable potency. Also, since naturally occurring polysaccharide must be isolated from a pathogen, safety concerns must be addressed with respect to both manufacture and use of the vaccine.

Attempts have been made to make the polysaccharide into a better immunogen. The polysaccharide or fragments thereof have been covalently coupled with various immunogenic proteins, such as diphtheria or tetanus toxoids. See, for example, U.S. Pat. No. 4,673,574 issued Jun. 16, 1987 to Anderson, U.S. Pat. No. 4,808,700 issued Feb. 28, 1989 to Anderson, et al., European Patent Office Publication No. 0 245 045 dated Nov. 11, 1987, and European Patent Office Publication No. 0 098 581 dated Jan. 18, 1984, all of which are incorporated herein by reference.

Several of the conjugate vaccines have been shown to be safe and more immunogenic than the conventional polysaccharide vaccines in children, particularly infants. The data suggest that the conjugate vaccines are functioning as T-cell dependent antigens. A T-cell-dependent response provides for a better overall immune response in a patient. One of the conjugate vaccines has been approved in the United States for children 15–18 months of age. Two of the conjugate vaccines have been licensed in the United States for infants as young as two months old.

The vaccines currently available to the medical practitioner have several major limitations. First, they do not protect against other Hi infections besides Hib. The polysaccharide is not found in non-typable *H. influenzae;* therefore, antibodies to it are non-protective against these strains. Second, they raise problems with respect to reproducibility, potency, and safety.

There are several avenues of on-going research on ways to overcome these limitations. One approach has been to develop procedures for Hib polysaccharide synthesis. The Hib capsule consists of a linear homopolymer of alternating molecules of ribose and ribitol joined by a phosphodiester linkage represented by the following formula:

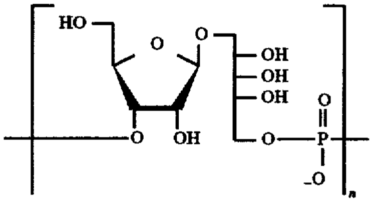

The polymer is known as polyribosylribitol phosphate and abbreviated PRP.

The PRP obtained from natural sources is crude degraded polysaccharide. It varies in molecular weight between 200 KD and 200,000 KD.

A few groups have been able to synthesize small PRP oligosaccharides. For example, European Patent Office Publication 0 320 942 dated Jun. 21, 1989, incorporated herein by reference, discloses the synthesis of synthetic PRP oligosaccharides of 2–20 units and their covalent attachment to immunogenic proteins, specifically tetanus or diptheria toxins or toxoids. The oligosaccharides are linked to the proteins through a spacer. A phosphite triester synthetic procedure was used for the oligomerization. European Patent Office Publication 0 276 516 dated Aug. 3, 1988, incorporated herein by reference, also discloses synthetic PRP oligosaccharides 2–20 monomers in length, their conjugation to carrier proteins, and the use of the conjugates as vaccines against Hib. The oligosaccharides are prepared using the phosphotriester synthetic procedure for oligomerization. Both of these involved solution-type synthetic techniques for the preparation of the PRP oligosaccharides.

Elie, et al., *Recl. Trav. Chim. Pays-Bas,* 108: 219–223 (1989), incorporated herein by reference, discloses the solid-phase synthesis of a PRP hexamer. The units were coupled using a phosphite triester method and controlled-pore glass as the solid support.

The use of synthetic PRP fragments should provide several advantages over the PRP obtained from natural sources. Synthetic PRP is chemically well-defined and characterized. It would be of superior quality and less prone to produce side effects in humans. Its use would also obviate problems relating to reproducibility, potency, and safety associated with PRP obtained from natural sources. In addition, while the naturally occurring PRP is generally cross-linked to the protein carrier at random points along its chain, synthetic PRP can be conjugated through a single point, which creates less undesired epitopes.

This research promises improvements to existing vaccines, but there are still drawbacks. First, the PRP synthesis is complicated and relatively inefficient. Thus, there is a need for improved synthesis procedures. Second, these improvements will be limited to vaccines against Hib.

Another approach has been to focus on the protein. There are some available data suggesting that the protein and the carbohydrate parts of the conjugate vaccines act as independent immunogens. Therefore, the choice of the protein component becomes important in seeking to enhance immunogenicity. It would be more desirable to have an immunogenic protein or polypeptide derived from *H. influenzae* as the protein component rather than a "nonsense" protein.

At least one group has conjugated an Hib outer membrane protein to PRP fragments. See European Patent Office Publication No. 0 338 265, dated Oct. 25, 1989, incorporated herein by reference. This application discloses 38 and 40 KD outer membrane proteins of Hib and their isolation and purification. The two proteins are quite similar. They are known as protein 2 (P2) or protein b/c because they occur as a doublet. The molecular weight depends upon the strain from which they are obtained. They are cross-reactive, have very similar amino acid compositions, and have the same amino and carboxy terminal sequences. The proteins are coupled to PRP fragments by reductive amination. The PRP fragments are obtained from naturally occurring PRP using standard techniques. The application states that the carrier proteins themselves may confer immunity.

This approach also suffers from certain limitations. The outer membrane proteins may vary among Hib types or serotypes within a particular type. Granoff, et al., in S. H. Sell and P. F. Wright (ed.), *Haemophilus Influenzae: Epidemiology, Immunology, and Prevention,* (New York: Elsevier Biomedical (1982)). Therefore, a vaccine based upon a particular outer membrane protein may not be effective against the broader spectrum of pathogenic *H. influenzae* bacteria and may not even be effective against all strains of Hib.

Others have focused on Hi proteins and peptides alone as vaccine candidates. For example, see PCT Publication No. WO 90/02557, published Mar. 22, 1990, incorporated herein by reference. This application discloses two antigenically related Hi outer membrane proteins with a molecular weight of about 16 KD. It further discloses related fusion proteins and peptide fragments of the outer membrane proteins, methods of purifying the proteins, and methods of making them by genetic engineering. All of these are claimed to be useful as immunogens in vaccines. Such vaccines will also have the drawbacks mentioned immediately above.

Clearly, there is a pressing need for a safe vaccine that is effective against both invasive and non-invasive *H. influenzae,* particularly in infants 2–6 months old. This ideal vaccine would also be effective against a wide variety of strains within each of the two categories by eliciting antibodies against a determinant found on the surface of most or all strains of *H. influenzae.*

The present invention overcomes the limitations of the existing technology and meets that need. It provides a novel synthetic PRP conjugated to newly isolated and purified *H. influenzae* adhesin proteins.

The ability to use an adhesin protein in a vaccine against *H. influenzae* is extremely desirable. Because of the way they function, adhesin proteins are believed to be highly conserved among strains of a particular type of bacteria. This is because they are the protein molecules that mediate attachment by bonding bacteria to host cells, the initial step in the infection process. Thus, the adhesins would be expected to be present in all strains (both encapsulated and unencapsulated) of Haemophilus. Therefore, the present vaccine would be effective against a broad array of types and strains of Hi. In addition, vaccines based upon adhesin proteins should be more effective than those based upon other outer membrane proteins, even for those bacterial strains from which the outer membrane proteins are derived. Antibodies to the adhesin protein would prevent adherence of the bacteria to the tissue of the host animal. Adherence is the initial step in Hi infection. Stopping the infection at this point would be the best approach possible.

The novel PRP of the invention also has advantages over the existing technology. It is better defined and characterized, and it is of superior quality when compared to PRP obtained from natural sources. Also, it has been more efficiently produced than the synthetic PRP described above.

SUMMARY OF THE INVENTION

It is an object of the invention to provide an immunogenic oligosaccharide-*H. influenzae* adhesin protein conjugate and a method for making it.

Another object of the invention is to provide a vaccine for protecting a mammal against *H. influenzae.*

Yet another object of the invention is to provide a method of inducing an immune response to *H. influenzae* in a mammal.

A further object of the invention to provide purified *H. influenzae* adhesin proteins.

A still further object of the invention is to provide a purified polypeptide capable of eliciting an antigenic response to *H. influenzae* in an animal host.

Yet another object of the invention is to provide methods for producing purified *H. influenzae* adhesin proteins.

A further object of the invention is to provide DNA coding for the adhesin proteins and derived polypeptides, vectors containing the DNA, microorganisms transformed by such DNA and vectors, and methods for preparing such materials.

A still further object of the invention is to provide a composition of matter consisting essentially of synthetic PRP oligosaccharides having the same number of monomeric units and a method of preparing the synthetic PRP.

Another object of the invention is to provide compounds useful as intermediates in the preparation of synthetic PRP and methods of preparing such compounds.

Additional objects and advantages of the invention will be set forth in part in the description that follows, and in part will be obvious from the description, or may be learned by the practice of the invention. The objects and advantages of the invention will be attained by means of the instrumentalities and combinations particularly pointed out in the appended claims. To achieve the objects and in accordance with the purpose of the invention, as embodied and broadly described herein, the present invention provides an immunogenic oligosaccharide-protein conjugate useful in a vaccine for protecting a mammal against *H. influenzae*. The conjugate is made up of a PRP fragment, preferably a synthetic oligosaccharide, coupled to an *H. influenzae* adhesin protein. Preferably, the oligosaccharides contain from 2–30 ribosylribitol phosphate monomers, and from 1–30 of such oligosaccharides are attached to the protein. In an alternative embodiment, the oligosaccharide is bound to a polypeptide that is an active site of the adhesin protein.

Preferably, the conjugate is represented by the following formula:

rial is separated from the insoluble material and contacted with receptors for the adhesin protein for period of time sufficient for the protein molecules to bind to the receptors. The receptors are attached to an insoluble solid support. As a result, the protein is separated from the solubilized material. The protein molecules are then removed from the receptors thereby being recovered in purified form.

In another embodiment, the adhesin proteins and related polypeptides of the invention are preferably recombinant proteins and polypeptides that have been produced through genetic engineering techniques. They are produced by an appropriate host cell that has been transformed by DNA that codes for such proteins or polypeptides.

An isolated or substantially pure DNA sequence that codes for the adhesin proteins of the invention is obtained as follows. Adhesin protein receptors or antibodies to the adhesin, preferably monoclonal antibodies, are used to screen a genomic library containing *H. influenzae* DNA. The library is made of clones which contain different sequences of the DNA which have been operably and recoverably inserted into a vector, with each of the vectors containing only one sequence of the DNA. The monoclonal antibodies or receptors identify the clones that produce the adhesin. The clone is then isolated. Preferably, the exogenous DNA sequences are recovered from the clone.

The invention further comprises isolated or substantially purified DNA derived from this DNA, for example, by single or multiple mutations. Preferably, such DNA hybrid-

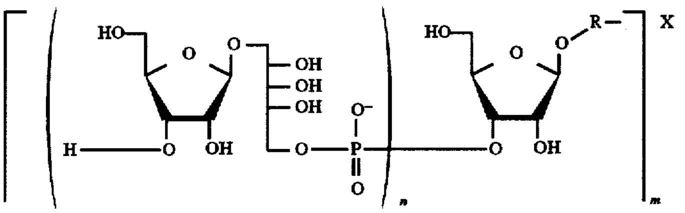

where m is 1-30, n is 2–30, R is $(CH_2)_pCH_2NH$ or $(CH_2CH_2O)_pCH_2CH_2NHCSNH$ where p is an integer from 1-3, and X is an *H. influenzae* adhesin protein or a fragment thereof containing an active site of the protein.

The vaccine comprises an immunologically effective amount of the conjugate in a pharmaceutically acceptable carrier. Preferably, the vaccine also contains an adjuvant. The administration of the vaccine or conjugate to a human or other mammal induces a T-cell dependent protective immune response.

The invention further comprises an isolated and a purified *H. influenzae* adhesin protein and modified proteins and polypeptides derived from the adhesin protein, provided such derived proteins and polypeptides are immunologically cross-reactive with the adhesin protein. Preferably, such derivatives are one or more epitopes of the adhesin protein. In a particularly preferred embodiment, the epitope is also a receptor binding site. The proteins and polypeptides may also be used in vaccines without being conjugated to the synthetic PRP.

In one embodiment, the adhesin protein is a minor *H. influenzae* outer membrane protein with a molecular weight of about 41,000 daltons. In another preferred embodiment, the adhesin protein is an *H. influenzae* outer membrane protein with a molecular weight of about 47,000 daltons.

In one embodiment, the adhesin protein is purified from *H. influenzae* bacteria. Hi membranes are solubilized. The solubilized material contains the adhesin protein. This mateizes with the DNA obtained from the genomic library under conditions of high stringency.

The invention further comprises a synthetic PRP oligosaccharide represented by the following formula:

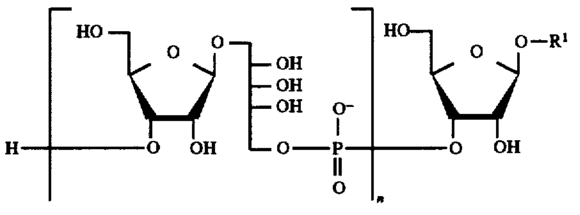

where n is an integer from 2 to 30 and $R^1$ is $(CH_2)_pCHO$ or $(CH_2CH_2O)_pCH_2CH_2NH_2$ where p is an integer from 1 to 3.

In still another embodiment, the invention provides a compound useful as an intermediate in the preparation of synthetic PRP of the invention. It is represented by the formula:

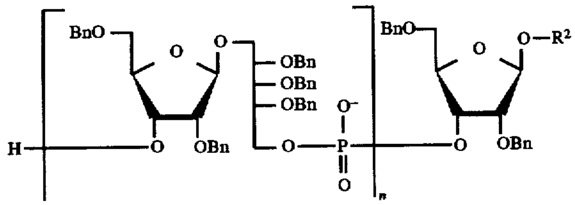

where n is an integer from 2 to 30, Bn is benzyl, and $R^2$ is $(CH_2)_pCH(OR^3)_2$ or $(CH_2CH_2O)_pCH_2CH_2R^4$ where p is an integer from 1 to 3, $R^3$ is an alkyl group 1–4 carbons in length, and $R^4$ is a group that can be converted into an amino group.

This compound is prepared using a solid phase synthesis. The monomer for chain initiation is a compound represented by the following formula:

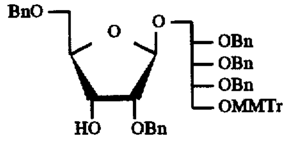

where Bn is benzyl and MMTr is monomethoxytrityl. This monomer is coupled to a solid phase and then detritylated. The resulting detritylated compound is coupled with a monomer for chain elongation represented by the formula:

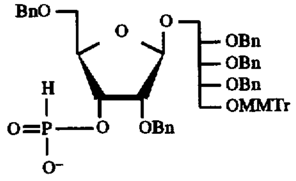

where Bn is benzyl and MMTr is monomethoxytrityl. The resulting compound is then detritylated. The chain elongation and detritylation steps are repeated a sufficient number of times until an oligomer of the desired length is obtained. The chain terminating monomer is then added. The chain terminating monomer is represented by the formula:

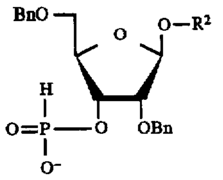

where Bn is benzyl and $R^2$ is $(CH_2)_pCH(OR^3)_2$ or $(CH_2CH_2O)_pCH_2CH_2R^4$ where p is an integer from 1 to 3, $R^3$ is an alkyl group 1–4 carbons in length, and $R^4$ is a group that can be converted into an amino group. The phosphonate groups of the support-bound oligomer are then oxidized to form phosphate groups. The resulting compound is then removed from the solid support and recovered.

The protective groups on this intermediate are then removed by hydrogenation. Where $R^2$ is $(CH_2CH_2O)_pCH_2CH_2R^4$, this results in the synthetic PRP of the invention. In the case where $R^2$ is $(CH_2)_pCH(OR^3)_2$, the hydrogenated compound is further subjected to selective acid hydrolysis.

The preferred conjugate of the invention is then prepared by coupling the synthetic PRP with the Hi adhesin protein by reductive amination where $R^1$ is $(CH_2)_pCHO$ or, where $R^1$ is $(CH_2CH_2O)_pCH_2CH_2NH_2$, by preparing the corresponding isothiocynate and then coupling the isothiocynate with the protein.

The accompanying drawings, which are incorporated into and constitute a part of this specification, illustrate one embodiment of the invention and, together with the description, serve to explain the principles of the invention.

BRIEF DESCRIPTION OF THE DRAWINGS

FIGS. 7A–7D show the nucleotide sequence of hin47 (SEQ ID NO:1) and the deduced Hin47 amino acid sequence (SEQ ID NO:2). The nucleotide sequence is numbered above each line and the deduced Hin47 amino acid sequence is shown below the line. The open reading frame for the hin47 gene is between nucleotide 115 and 1503. The end of the putative leader sequence and beginning of the putative mature polypeptide is indicated at nucleotide base 189. The predicted molecular weight of the mature polypeptide is 46399 and it has a pI of 5.86.

DETAILED DESCRIPTION OF THE INVENTION

Figure 1:
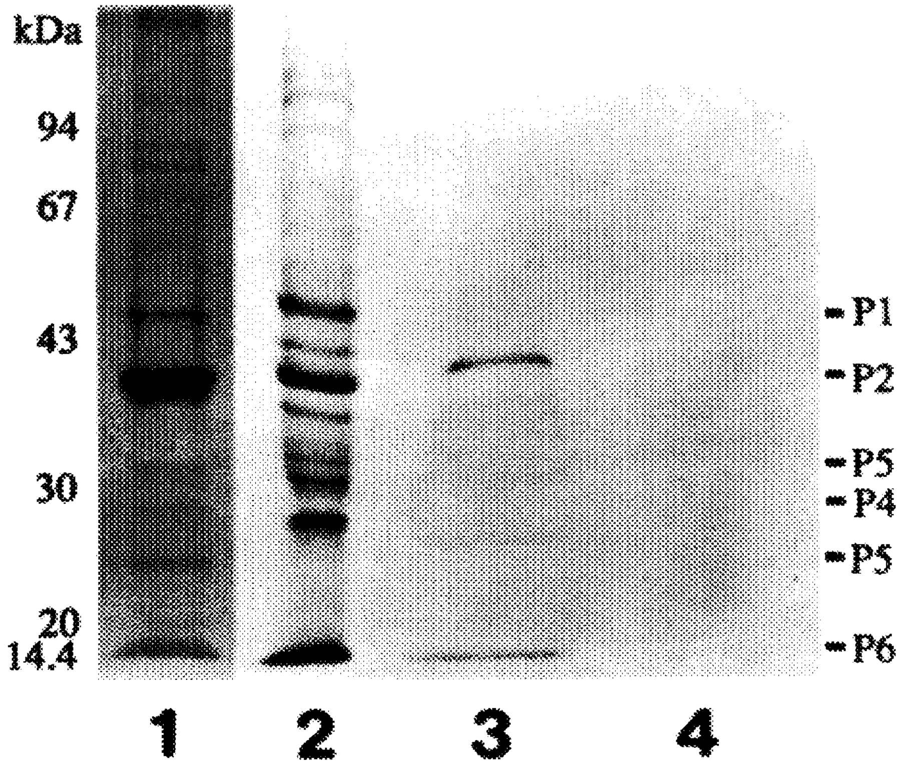
FIG. 1 shows an analysis of outer membrane preparations by SDS-polyacrylamide gel electrophoresis. Samples included the following (lanes): 1, total outer membrane protein preparation from *Haemophilus influenzae* type b stained with Coomassie blue; 2, autoradiography of $^{35}S$-labeled total outer membrane proteins; 3, autoradiography of $^{35}S$-labeled adhesin protein eluted from immobilized receptor asialo-$GM_1$; 4, autoradiography of material eluted from immobilized globoside, a nonsense glycolipid. Arrow indicates the adhesin migrating between P1 and P2 with a molecular weight of about 41 kD.

Reference will now be made in detail to the presently preferred embodiments of the invention, which, together with the following examples, serve to explain the principles of the invention.

The invention comprises an immunogenic oligosaccharide-*H. influenzae* adhesin protein conjugate useful as a vaccine against *H. influenzae*, purified *H. influenzae* adhesin proteins and related proteins and polypeptides, DNA coding for the proteins and polypeptides, host cells containing the DNA and producing the proteins and polypeptides, synthetic PRP oligosaccharides and intermediates useful for their synthesis, and methods of making and using these materials.

Immunogenic Congate

The conjugate comprises a polyribosylribitol phosphate fragment chemically coupled to a purified *H. influenzae* adhesin protein. Preferably, the PRP fragment is a synthetic oligosaccharide. From 1 to about 30 and preferably from about 5 to 20 of the natural fragments or synthetic oligosaccharides are attached to the protein.

The fragments are attached to the protein by known techniques for covalently attaching polysaccharides to proteins or polypeptides, applied to the teachings contained herein. The preferred techniques here are reductive amination or isothiocyanate coupling.

Any adhesin protein may be used. In one embodiment, the purified adhesin protein is a minor Hi outer membrane protein with a molecular weight of about 41,000 daltons, distinct from P1 or P2.

In another preferred embodiment, the purified adhesin protein is an Hi outer membrane protein with a molecular weight of about 47,000 daltons, distinct from P1–P6.

Alternatively, the protein may be replaced by a polypeptide that is an active site of the adhesin protein. As used herein, the term "active site" means an epitope (antigenic determinant) or an *H. influenzae* receptor binding site, which may or may not also be an epitope. As used herein, the term "receptor" is a macromolecule that binds to an Hi adhesin protein. The macromolecule is preferably a glycosphingolipid. Without intending to limit the scope of the invention, it is believed that the binding site is an epitope.

When the PRP fragment is obtained from natural sources, it is of varying lengths, but preferably about 8 to 120 monomers in length. Such fragments are obtained by known techniques, such as those described in the above-referenced European Patent Office Publication No. 0 338 265.

Synthetic PRP is a linear homopolymer of alternating molecules of ribose and ribitol joined by a phosphodiester linkage and represented by the formula:

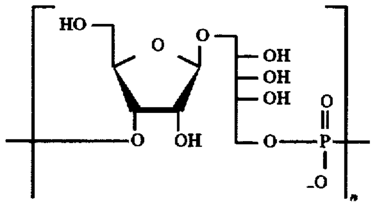

where n is 2 to 30 and preferably 5–20. Such synthetic PRP's include those known in the art as well as the novel ones of the invention. For example, the previously mentioned European Patent Office Publications 0 320 942 and 0 276 516 disclose synthetic PRP's that could be used in the conjugate of the invention.

Preferably, the synthetic PRP is a compound represented by the formula:

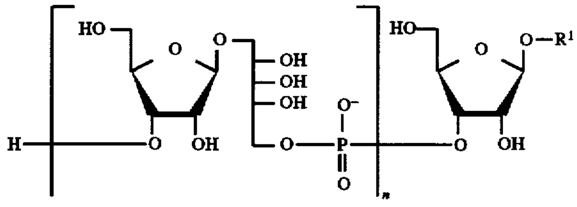

where n is an integer from 2 to 30 and $R^1$ is $(CH_2)_pCHO$ or $(CH_2CH_2O)_pCH_2CH_2NH_2$ where p is an integer from 1 to 3. Preferably n is 5–20 and p is 1. The synthetic PRP will be associated with a counter ion. Preferably, the ion is sodium ($Na^+$).

The synthetic oligosaccharides usually contain a chemical spacer or linker by which they are attached to the protein. Such a spacer may be any chemical linkage that serves to connect the PRP and the protein and that has limited or no adverse effect to the animal host when the conjugate is administered. Such spacers may include those known in the art as well as the novel spacers of the invention. Known spacers include those disclosed in the previously mentioned European Patent Office Publications 0 320 942 and 0 276 516 as well as those disclosed in U.S. Pat. 4,830,852 issued May 16, 1989 to Marburg, et al., the latter of which is incorporated herein by reference. Preferably, the chemical spacer is a moiety represented by the formula:

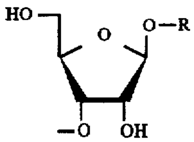

where R is $(CH_2)_pCH_2NH$ or $(CH_2CH_2O)_pCH_2CH_2NHCSNH$ and p is an integer from 1–3, preferably 1.

In the most preferred embodiment of the invention, the conjugate is represented by the following formula:

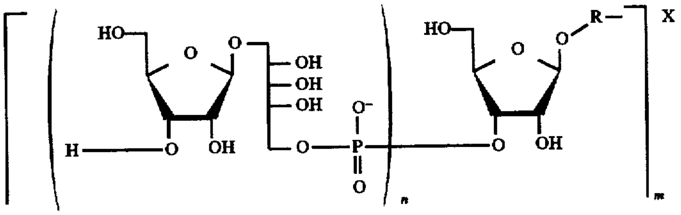

where m is 1–30, n is 2–30, R is $(CH_2)_pCH_2NH$ or $(CH_2CH_2O)_pCH_2CH_2NHCSNH$ where p is integer from 1–3, and X is an *H. influenzae* adhesin protein or a fragment thereof containing an active site of the protein. Preferably, m is 5–20, n is 5–20, and p is 1. The symbol X in the above-referenced formula may also represent certain derived or modified proteins or polypeptides discussed below. The conjugate will be associated with a counter ion. Preferably, the ion is $Na^+$.

Adhesin Proteins

The invention further comprises an isolated *H. influenzae* adhesin protein. As used herein, in this context, the term "isolated" means that the protein is significantly free of other proteins. That is, a composition comprising the isolated protein is between 70% and 94% pure by weight. Preferably, the protein is purified. As used herein, the term "purified" and related terms means that the protein is at least 95% pure by weight, preferably at least 98% pure by weight, and most preferably at least 99% pure by weight. The protein binds to a receptor selected from the group consisting of fucosylasialo-GM1, asialo-GM1, and asialo-GM2, all of which contain the structure N-acetylgalactosamine(beta 1–4)galactose(beta 1–4)glucose-(beta 1–1)ceramide abbreviated GalNAc(beta1–4)Gal(beta1–4)Glc(beta1—1)Cer. The protein also binds to another receptor, phosphatidylethanolamine.

In one embodiment, the protein is a minor outer membrane protein with a molecular weight of about 41 KD as determined by SDS PAGE. It is distinguishable from the various major outer membrane proteins that have been identified for Hi. In particular, the protein appears as a fainter band between the bands on a polyacrylamide gel for the outer membrane proteins known as P1 and P2. See FIG. 1.

This purified Hi adhesin protein is prepared preferably from natural sources as follows. Hi bacterial membranes are obtained by standard techniques and solubilized, using a solubilizing compound, such as a detergent. Preferably, the membranes are mixed with the detergent, and the mixture is sonicated. The most preferred solubilizing agent is a solution containing about 1.0% to about 1.5% and preferably about 1.3% octylglucopyranoside. The adhesin protein is in the solubilized material. The remaining insoluble material from the membrane is separated, preferably by centrifuging.

The supernatant is contacted with receptors that bind the protein and are attached to an insoluble solid support or matrix, such as a microtiter well or a gel, for a period of time and under conditions sufficient for the protein to bind to the receptors, thus separating the protein from the other material. The preferred receptors for the adhesin protein are fucosylasialo-GM1, asialo-GM1, asialo-GM2, and phosphatidylethanolamine. These receptors can be prepared in accordance with the procedures disclosed in Krivan, et al., *Proc. Natl. Acad. Sci. USA*, 85: 6157–6161 (1988), incorporated herein by reference. The most preferred receptor, asialo-GM1, is also commercially available. All of these receptors, except phosphatidylethanolamine, contain the carbohydrate sequence GalNAc(beta1–4)Gal(beta1–4)Glc, which, accordingly, may also be used as a receptor for the purification of the adhesin protein. This sequence can be prepared using standard carbohydrate synthesis techniques.

The adhesin protein is then eluted using the appropriate agent. This may be free receptor in solution, SDS elution buffer, or a chaotropic agent, such as KSCN, NaCl, or quanidine hydrochloride. The eluted protein is then tested against the receptor to confirm that the protein does bind to it. The purity of the isolated protein is analyzed by SDS-PAGE. Preferably, it will be about 99% pure after affinity purification with the most preferred receptor.

For purification of larger amounts of the adhesin protein, chromatography is preferred. The receptor is immobilized onto a hydrophobic gel support, such as octyl-agarose. This matrix is prepared by adsorbing the receptors to the hydrophobic gel in the presence of salt as described by Hirabayashi, et al. for other glycolipids. Hirabayashi, et al., *J. Biochem.*, 94: 327–330 (1983), incorporated herein by reference. Photoactivatable heterobifunctional crosslinking agents have also been used to prepare glycolipid affinity matrices. Lingwood, C., *J. Lipid Res.*, 25: 1010–1012 (1984), incorporated herein by reference. In this case, the receptor-active lipid is covalently crosslinked to the gel support. The column is then preferably washed extensively with an appropriate buffer solution, such as TMS-buffer saline, before the protein is eluted.

A more preferred method is to purify the adhesin by affinity chromatography using an anti-adhesin monoclonal or polyclonal antibody prepared by standard techniques. In this case, the antibodies are covalently linked to agarose gels activated by cyanogen bromide or succinamide esters (Affi-Gel, BioRad Inc.) or by other methods known by those skilled in the art. The sonic extract is loaded on the top of the gel as described above.

In another preferred embodiment, the adhesin proteins comprise an *H. influenzae* outer membrane protein with a molecular weight of about 47,000 daltons. FIGS. 7A and 7B show the protein amino acid sequence as well as the designated nucleotide sequence of the open reading frame (ORF) encoding a 49 kDa protein. The 49 kDa protein comprises 463 amino acids (amino acids 1–463 in FIG. 7A and 7B), includes a putative signal sequence of approximately 2.5 kDa and 25 amino acids, thereby resulting in a mature protein of approximately 47 kDa and 438 amino acids (amino acids 26 through 463 on FIG. 7A and B), herein designated Hin47. This protein is distinguishable from the known Hi proteins P1–P6 on the basis of molecular weight and the fact that those proteins are integral membrane proteins, while this protein is an outer membrane protein. This protein also binds to the previous mentioned receptors as well as to sulfatide, ($SO_3^-$-galactose(beta 1-1)ceramide) and it is soluble in 1% Sarkosyl (N-lauroylsarcosine).

This protein is preferably prepared in purified form as follows. Hi membranes are extracted with a solution that removes membrane associated proteins, which produces an extract containing the adhesin protein along with other membrane associated proteins. Preferably, this solution is a nonionic detergent, such as Sarkosyl or octylglucopyranoside. The insoluble material is separated from the extract, preferably by centrifugation. This produces a supernatant that contains the adhesin protein. The supernatant is then brought into contact with a monoclonal antibody which recognizes the adhesin protein. The antibody is bound to an insoluble solid support. The contact is for a period of time and under standard reaction conditions sufficient for the adhesin protein to bind to the monoclonal antibody. Preferably, the solid support is a material used in a chromatographic column. The adhesin protein is then removed from the antibody, thereby permitting the recovery of protein in purified form. Preferably, the nonionic detergent solution is removed from the supernatant before the supernatant is subjected to the affinity chromatography. Such removal is preferably accomplished by dialyzing the supernatant to produce a dialysate that is substantially free of the detergent.

The monoclonal antibodies can be prepared by standard techniques, given the teachings contained herein. Such techniques are disclosed, for example, in U.S. Pat. No. 4,271,145, issued Jun. 2, 1981 to Wands et al. and U.S. Pat. No. 4,196,265, issued Apr. 1, 1980 to Koprowski et al., both of which are herein by reference. Briefly, mice are immunized with Hi membranes. Hybridomas are prepared by fusing spleen cells from the mice with myeloma cells. The fusion products are screened for those producing antibodies that bind to the Hi membranes. The positive clones are then screened to identify those whose binding with the Hi membranes is inhibited by an Hi adhesin receptor. The positive hybridomas clones are isolated, and the monoclonal antibodies are recovered from those clones.

Alternatively, the outer membrane proteins could be separated on a gel. The 47 kDa band could be cut out and injected into the mice. The hybridomas could be prepared and screened as described above.

DNA

The adhesin proteins of the invention are preferably produced through genetic engineering techniques. In this case, they are produced by an appropriate host cell that has been transformed by DNA that codes for the proteins. Preferably, the host cell is a bacterium, and most preferably the bacterium is *E. coli*, *B. subtilis*, or Salmonella.

The DNA of the invention is an isolated or substantially purified DNA sequence (i.e., polydeoxyribonucleotide molecule) encoding a protein or polypeptide that binds to the previously mentioned receptors. Preferably, the DNA of the invention includes an open reading frame (ORF) sequence (nucleotides 115 through 1503 in FIGS. 7A and B), designated hin47, encoding an approximate 49 kDa and 463 amino acid protein, designated Hin47, as shown in FIGS. 7A and B. Most preferably, the DNA comprises that part of the ORF that does not code for the signal sequence (nucleotides 191 through 1503 in FIGS. 7A and B). As used herein, the term "isolated" and variations thereof means that the DNA is in isolation from DNA encoding other proteins or polypeptides normally accompanying the Hi adhesin proteins. Thus, the DNA of the invention includes DNA encoding the protein or polypeptide when that DNA has been cloned into a microbial vector, such as a plasmid, or into a viral vector that may be harbored by a bacteriophage, provided that such clones are isolated from clones that contain DNA encoding other proteins or polypeptides normally accompanying this one. As used herein, the term "substantially pure" and variants thereof means that the DNA is substantially free of DNA and RNA that does not encode the proteins or polypeptides of the invention. That is, there will be no more than about 1% by weight of other DNA and RNA and preferably no more than about 0.2% by weight of other DNA and RNA in any sample that contains the DNA of the invention.

Preferably, the DNA is obtained by using either the receptors or monoclonal antibodies to the adhesins to screen an appropriate genomic library that contains *H. influenzae* DNA. Such a library comprises colonies of a single type of microorganism, generally bacteria like *E. coli* K12 (XL-1), into which pieces of the foreign DNA have been inserted, generally by being incorporated into a plasmid, cosmid, or phage vector compatible with the microorganism. More specifically, the library comprises clones of vectors into which different sequences of the DNA have been operably and recoverably inserted, each of the vectors containing only one sequence of the DNA. The vectors may be plasmids, cosmids, phagemids, or phage genomes. If necessary because of the type of library being used, segments of DNA will have been inserted into the vectors in a manner that they will be expressed under appropriate conditions (i.e., in proper orientation and correct reading frame and with appropriate expression sequences, including an RNA polymerase binding sequence and a ribosomal binding sequence.) The microorganisms will be ones that do not express the adhesin protein, such as *E. coli* HB101.

Clones from the library are brought into contact with the receptors or antibodies to identify those clones that bind. The clones are isolated and the exogenous DNA sequence is recovered from one of the clones. The sequence is preferably evaluated to determine if it encodes the protein.

Preferably, the genomic library comprises bacteria, such as *E. coli* infected by phage, preferably bacteriophage lambda. Plaques produced by the phage infected bacteria are screened by monoclonal antibodies to identify those plaques containing bacteria that produce the adhesin protein. The screening involves contacting the plaques with the monoclonal antibody to determine if binding has occurred, using standard techniques. Preferably, immunoassays are used.

In this preferred embodiment, the positive clones are then isolated by purifying the positive plaques and inducing plasmid formation in the bacteria in the purified plaque with a helper phage according to standard techniques.

In an alternate preferred embodiment, colonies containing DNA that encodes an Hi adhesin protein could be detected using DYNA Beads according to Olsvick et al., 29th ICAAC, Houston, Tex. 1989, incorporated herein by reference. The previously described receptors would be crosslinked to tosylated DYNA Beads M280, and these receptor-containing beads would then be used to adsorb to colonies expressing the adhesin protein. Colonies not expressing the adhesin would be removed by washing, and this process would be repeated to obtain an appropriate enrichment. Putative adhesin expressing colonies would then be plated and confirmed by metabolically labeling each colony with 35S-methionine and testing the ability of the colony to bind to the receptor as previously described. The DNA from several adherring clones would be compared to identify shared sequences, and these shared sequences would be further subcloned and characterized.

Alternatively, the receptors could be nonspecifically immobilized to a suitable support, such as silica or Sealite resin. This material would then be used to adsorb to colonies expressing the adhesin protein as described in the preceding paragraph.

In another alternate preferred embodiment, the gene for a specific adhesin would be localized and identified by constructing non-adherent mutants of a specific pathogen. This would be accomplished by creating mutants using a transposable element such as TnPhoA as described in Manoil et al., *Proc. Natl. Acad. Sci. USA*, 82: 81129–81133 (1985), incorporated herein by reference. Alkaline phosphatase positive mutants would indicate mutations within exported proteins. Since the adhesin for each pathogen is located on the outer membrane surface and therefore exported, this set of mutants would contain a much reduced subset of mutants. They would then be screened for a loss in binding activity.

It will be recognized by persons skilled in the art that a DNA sequence for an Hi adhesin protein can be modified by known techniques in view of the teachings disclosed herein. For example, different codons can be substituted that code for the same amino acid as the original codon. Alternatively, the substitute codons may code for a different amino acid that will not affect the immunogenicity of the protein or which may improve its immunogenicity. For example, oligonucleotide directed, site specific mutagenesis or other techniques to create single or multiple mutations, such as replacements, insertions, deletions, and transpositions, as described in Botstein and Shortle, "Strategies and Applications of In Vitro Mutagenesis," *Science*, 229: 1193–1210 (1985), which is incorporated herein by reference, can be employed. Since such modified DNA can be obtained by the application of known techniques to the teachings contained herein, such DNA is within the scope of the claimed invention.

Moreover, it will be recognized by those skilled in the art that the DNA sequence (or fragments thereof) of the invention can be used to obtain other DNA sequences that hybridize with it under conditions of moderate to high stringency (including the derived sequences discussed in the preceding paragraph), using general techniques known in the art. That is, the hybridizing sequences are at least 90% homologous and preferably at least 95% homologous to hin47. Accordingly, the DNA of the invention includes such DNA.

The DNA of the invention may be used in accordance with known techniques, appropriately modified in view of the teachings contained herein, to construct an expression vector, which is then used to transform a microorganism for the expression and production of the adhesins of the invention. Such techniques include those disclosed in U.S. Pat. No. 4,440,859 issued Apr. 3, 1984 to Rutter et al., U.S. Pat. No. 4,530,901 issued Jul. 23, 1985 to Weissman, U.S. Pat. No. 4,582,800 issued Apr. 15, 1986 to Crowl, U.S. Pat. No. 4,677,063 issued Jun. 30, 1987 to Mark et al., U.S. Pat. No. 4,678,751 issued Jul. 7, 1987 to Goeddel, U.S. Pat. No. 4,704,362 issued Nov. 3, 1987 to Itakura et al., U.S. Pat. No. 4,710,463 issued Dec. 1, 1987 to Murray, U.S. Pat. No. 4,757,006 issued Jul. 12, 1988 to Toole, Jr., et al., U.S. Pat. No. 4,766,075 issued Aug. 23, 1988 to Goeddel, et al., and U.S. Pat. No. 4,810,648 issued Mar. 7, 1989 to Stalker, all of which are incorporated herein by reference.

The DNA of the invention may be joined to a wide variety of other DNA sequences for introduction into an appropriate host cell. The companion DNA would depend upon the nature of the host cell, the manner of the introduction of the DNA into the host cell, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques.

Generally, not all of the hosts will be transformed by the vector. Therefore, it will be necessary to select for transformed host cells. Once selection technique involves incorporating into the expression vector a DNA sequence, with any necessary control elements, that codes for a selectable trait in the transformed cell, such antibiotic resistance. Alternatively, the gene for such selectable trait can be on another vector, which is used to co-transform the desired host cell. The preferred expression vector for use in the invention is the plasmid pMC101. The preferred host cell is *E. coli.*

The transformed host cells express the proteins or polypeptides of the invention. Such cells are cultured by known techniques, and the proteins or polypeptides are recovered by known techniques. Depending upon the host and expression system used, the recombinant proteins and polypeptides of the invention may be part of a fusion protein produced by the transformed host cells. Such proteins are recovered by known techniques, and the undesired part may be removed by known techniques. Alternatively, the fusion protein itself may be more immunogenic than the recombinant protein or polypeptide alone and, therefore, may itself be used in a vaccine.

If desirable, the adhesins can be further purified by the application of standard protein purification techniques, modified and applied in accordance with the discoveries and teachings described herein. Such techniques include electrophoresis, centrifugation, gel filtration, precipitation, dialysis, chromatography (including ion exchange chromatography, affinity chromatography, immunoadsorbent affinity chromatography, reverse-phase high performance liquid chromatography, and gel permeation high performance liquid chromatography), isoelectric focusing, and variations and combinations thereof.

One or more of these techniques are employed sequentially in a procedure designed to separate molecules according to their physical or chemical characteristics. These characteristics include the hydrophobicity, charge, binding capability, and molecular weight of the protein. The various fractions of materials obtained after each technique are tested for their ability to react with the adhesin receptors. Those fractions showing such activity are then subjected to the next technique in the sequential procedure, and the new fractions are tested again. The process is repeated until only one fraction reactive with the receptors remains and that fraction produces only a single band when subjected to polyacrylamide gel electrophoresis.

The preferred techniques include those identified and described in U.S. Pat. No. 4,446,122 issued May 1, 1984 to Chu, et al., which is incorporated herein by reference. Preferably, the adhesins are purified by receptor affinity chromatography or antibody affinity chromatography.

Modified Adhesins

The adhesins of the invention may be modified by known protein modification techniques. Such modifications include breaking the protein into fragments that contain at least one active site or the addition, substitution, or deletion of one or more amino acids to the protein or a fragment thereof. Preferably, such derived proteins or polypeptides are immunologically cross-reactive with the Hi adhesin proteins, thus being capable of eliciting an antigenic response to *H. influenzae* in an animal host. Most preferably, such derived proteins or polypeptides also bind to an *H. influenzae* receptor selected from the group consisting of fucosylasialo-GM1, asialo-GM1, and asialo-GM2. (As used in this specification, the term "polypeptide" also includes shorter chains of amino acids that are often referred to as peptides.) Such modifications may enhance the immunogenicity of the protein or have no effect on such activity. The modification techniques include those disclosed in U.S. Pat. No. 4,526, 716, issued Jul. 2, 1985 to Stevens, incorporated herein by reference.

The proteins of the invention may contain one or more amino acid sequences that are not necessary to their immunogenicity. It may be the case, for example, that only the amino acid sequences of a particular epitope of the antigen will be necessary for immunogenic activity. Unwanted sequences can be removed by techniques well-known in the art. For example, unwanted amino acid sequences can be removed via limited proteolytic digestion using enzymes such as trypsin, papain, or related proteolytic enzymes.

This latter approach is expected to be particularly useful for the adhesin protein of the invention. Since the protein binds to several related receptors having a consensus sequence, the protein should have a well conserved region that acts as the receptor binding site. This site is the particularly preferred polypeptide of the invention.

Alternatively, polypeptides corresponding to various immunogenic epitopes and/or the receptor binding site of the protein may be chemically synthesized by methods well-known in the art, given the teachings contained herein. These include the methods disclosed in U.S. Pat. No. 4,290,944, issued Sep. 22, 1981 to Goldberg, incorporated herein by reference.

Modified proteins or polypeptides can be prepared that are substantially homologous to the Hi adhesin protein or to the polypeptides discussed above through the use of known techniques and routine experimentation in view of the teachings contained herein. As used herein, the term "substantially homologous" means immunologically cross-reactive. Such a protein or polypeptide may be identified by the fact that it will bind to antibodies that were made to the adhesin protein of the invention, which antibodies can be prepared by standard techniques. Some of such modified proteins or polypeptides may have enhanced immunogenicity compared to the one from which they are derived.

Thus, the invention includes a class of derived proteins and polypeptides, including synthetically derived peptides or fragments of the adhesin protein, having common elements of origin, structure, and mechanism of action, such as immunogenic effect or being able to bind to the previously mentioned receptors, that are within the scope of the present invention because they can be prepared by persons skilled in the art without undue experimentation, once given the teachings of the present invention. Moreover, since persons skilled in the art can make modifications to or derivatives of epitopes or the receptor binding site on the proteins or polypeptides of the invention, once such epitopes or site are identified, such modifications or derivatives are within the scope of the invention. Such derived proteins and polypeptides are preferably pure as that term was previously defined herein.

The Hi adhesin protein of the invention (as well as the related proteins and polypeptides derived therefrom) has utility not only in the conjugate vaccine but as an immunogen in its own right. Thus, it can be used in a vaccine for animals, including mammals, rodents, primates, and humans. The preferred use is a vaccine for humans, preferably children, and most preferably young infants.

Such a vaccine can be prepared by techniques known to those skilled in the art and would comprise, for example, the antigen, a pharmaceutically acceptable carrier, an appropriate adjuvant, and other materials traditionally found in vaccines. An immunologically effective amount of the antigen to be used in the vaccine is determined by means known in the art in view of the teachings herein.

Synthetic PRP

The invention further comprises novel synthetic PRP represented by the formula:

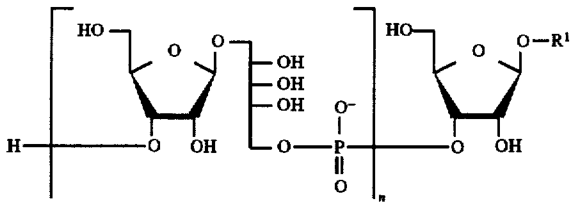

where n is an integer from 2 to 30, preferably 5–20, and $R^1$ is $(CH_2)_pCHO$ or $(CH_2CH_2O)_pCH_2CH_2NH_2$ where p is an integer from 1 to 3, preferably 1. The ability to prepare this novel synthetic PRP permits the preparation of compositions where all of the PRP oligosaccharides are of the same length (i.e., have the same number of monomeric units), in contrast to PRP obtained from natural sources, where the fragments vary tremendously in length.

The PRP of the invention is prepared by a combination of solid phase synthesis and the highly efficient H-phosphonate method for the construction of the phosphodiester linkage. It also involves the use of gels with higher levels of functionalization, which are better suited for commercial scale operations.

The general approach is to prepare a protected oligomeric ribosylribitol phosphate derivative by the following steps. First, the monomer for chain initiation is coupled to a solid phase. The monomer is represented by the formula:

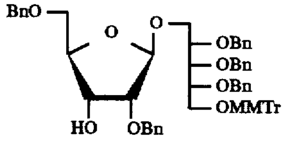

where Bn is benzyl and MMTr is monomethoxytrityl. See Compound 7, Table 1. The preferred solid phase is a Merrifield-type amino resin. The chain initiation monomer (Compound 7) is coupled to the solid phase by known techniques, such as reaction with succinic anhydride, followed by coupling of the obtained succinate of Compound 7 to amino groups of the solid phase. The loading is determined by colorimetric quantification of the trityl cation released on acid treatment. The coupled compound is then detritylated, such as by treatment with trifluoroacetic acid in dichloromethane.

Chain elongation is accomplished by coupling the detritylated chain initiation monomer with a compound represented by the formula:

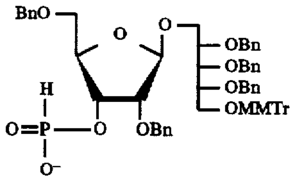

where Bn is benzyl and MMTr is monomethoxytrityl. See Compound 8, Table 1. (The compound will be associated with a counter ion. Preferably, the ion is an organic cation, such as triethyl ammonium.) The coupling is accomplished by using a condensing reagent, such as pivaloyl chloride. The resulting compound is then detritylated. The chain elongation-detritylation steps are repeated a sufficient number of times to prepare an oligosaccharide of the desired length. Thus, if n represents the desired number of PRP monomers in the oligosaccharide, the chain elongation-detritylation cycles are repeated n-2 times after the coupling of the chain initiation monomer and the first chain elongation monomer.

The chain is terminated by coupling it with a chain termination monomer represented by the following formula:

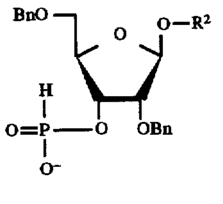

where Bn is benzyl and $R^2$ is $(CH_2)_pCH(OR^3)_2$ or $(CH_2CH_2O)_pCH_2CH_2R^4$ where p is 1–3, $R^3$ is an alkyl group 1–4 carbons in length, and $R^4$ is a group that can be converted into an amino group. See Compounds 10 and 12, Table 2. (The compound will be associated with a counter ion. Preferably, the ion is an organic cation, such as triethyl ammonium.) Preferably, p is 1, and $R^3$ is methyl or ethyl. Preferably, $R^4$ is $N_3$, trifluoroacetyl, benzyloxycarbonyl, or fluorenylmethoxycarbonyl.

The phosphonate groups of the solid-bound oligomer are then oxidized to form phosphate groups. Preferably, this is accomplished by treatment with iodine in aqueous pyridine.

The resulting compound is then removed from this solid support, preferably through cleavage by methanolysis. The recovered compound is represented by the formula:

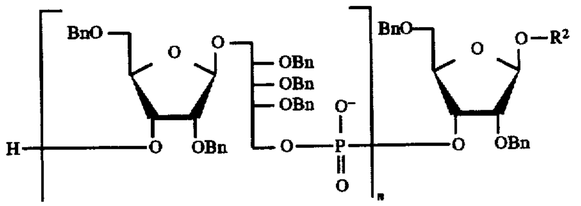

where n is an integer from 2 to 30, preferably 5–20, Bn is benzyl, and $R^2$ is defined as above. See Compounds 13 and 15, Table 3. (The compound will be associated with a counter ion. Preferably, the ion is ammonium or substituted ammonium.)

The resulting compound is then deprotected by hydrogenation with palladium on charcoal. In the case where $R^2$ is $(CH_2)_pCH(OR^3)_2$, the hydrogenated compound is further subjected to selective acid hydrolysis, such as by treatment with aqueous trifluoroacetic acid. The resulting PRP oligomers are purified by standard techniques, preferably by ion-exchange chromatography, HPLC or gel filtration. See Compounds 14 and 16, Table 3.

Table 1 shows the synthesis of the chain initiation monomer, Compound 7, and the chain elongation monomer, Compound 8. The readily available methyl 2,3-isopropylidene-beta-D-ribofuranoside (Compound 1) (Leonard, et al., *J. Het. Chem.* 3: 485 (1966), incorporated herein by reference) is used as starting material. Allylation of Compound 1 with allyl bromide/sodium hydroxide in N,N-dimethylformamide gives the expected 5-O-allyl Compound 2 as an oil that can be distilled. This compound is subjected to a sequence of reactions comprising hydrolysis with aqueous formic acid, sodium borohydride reduction, tritylation with triphenylmethylchloride/pyridine, benzylation with benzyl chloride/sodium hydroxide in N,N-dimethylformamide, and hydrolysis with aqueous acetic acid. The resulting Compound 3 is purified by silica gel chromatography.

Benzylation of Compound 1 with benzyl chloride/sodium hydroxide in N,N-dimethylformamide gives the expected 5-O-benzyl compound 4 as an oil that can be distilled. This compound is subjected to a sequence of reactions comprising hydrolysis with aqueous formic acid and benzoylation with benzoyl chloride in pyridine, giving Compound 5, which is purified by chromatography and crystallization. Compound 5 is subjected to a further sequence of reactions comprising treatment with hydrogen bromide in dichloromethane to prepare the glycosyl bromide, followed by treatment with methanol and collidine. The resulting orthoester is then debenzoylated with sodium methoxide in methanol. The resulting product is allylated with allyl bromide/sodium hydroxide in N,N-dimethylformamide to give, after purification by silica gel chromatography, Compound 6.

Glyosylation can be accomplished by several methods. In the preferred method (A), Compound 6 is treated with trimethylsilyl chloride to give the corresponding glycosyl chloride, which, when treated with Compound 3 in the presence of molecular sieves, gives a ribitol glycoside. Alternatively (B), Compound 6 is transesterified in the presence of Compound 3. The resulting ribitol orthoester is then rearranged in situ to give the ribitol glycoside.

The ribitol glycoside is then subjected to debenzoylation with sodium methoxide in methanol and benzylation with benzyl chloride/sodium hydroxide in N,N-dimethylformamide. The resulting 5O-allyl-2,3,4-tri-O-benzyl-1-O-(3-O-allyl-2,5-di-O-benzyl-beta-D-ribofuranosyl)-D-ribitol is deallylated by treatment with, successively, tris-(triphenylphosphine)rhodium(I)chloride and aqueous acetic acid and monomethoxytritylated with monomethoxytrityl chloride. The resulting chain initiation monomer (Compound 7) is purified by chromatography.

The condensation reaction of Compound 7 with phosphorous acid/5,5-dimethyl-2-oxo-2-chloro-1,3,2-dioxaphosphorinane gives the chain elongation monomer (Compound 8).

Table 2 shows the synthesis of the monomers for chain termination. Compound 6 is reacted with trimethylsilyl chloride to give the corresponding chloride, which is reacted with the appropriate alcohols in the presence of molecular sieves to give beta-glycosides of the alcohols. Preferably, the alcohols are 2-(2-azidoethoxy)ethanol, 2-[2-benzyloxycarbonylamido)ethoxy]ethanol, or 2,2-diethoxyethanol. The beta-glycosides are subjected to the reaction sequence debenzoylation, benzylation, and deallylation, as in the preparation of Compound 7, which gives Compounds 9 or 11. Condensation with phosphorous acid/5-5-dimethyl-2-oxo-2-chloro-1,2,3-dioxaphosphorinane according to the same procedure used to prepare Compound 8 gives the desired spacer-containing monomers (Compounds 10 or 12).

Table 3 shows the specific PRP oligomers obtained after solid phase synthesis employing Compounds 7, 8, and 10 or 12. Compounds 13 and 15 are the protected oligomers after removal from the solid support, and Compounds 14 and 16 are the final oligomers after deprotection.

The preferred use of the novel PRP is in the preparation of the novel immunogenic conjugates. The oligomer is coupled to one of the proteins or polypeptides of the invention by standard techniques applied to the teachings contained herein. When the spacer terminates in an aldehyde group, the preferred technique is reductive amination using sodium borohydride as described in Roy, et al., *J. Carbohydr. Chem.* 6: 161–165 (1987) and Lee, et al., *Carbohydr. Res.*, 77: 149–156 (1979), both of which are incorporated by reference. When the spacer terminates with an amino group, the PRP is converted into the isothiocynate by treatment with an activated thiocarbonic acid derivative, such as thiophosgene, and then coupled to the protein at a pH of 9–10 in accordance with the procedures described in Kallin, et al., *Glycoconjugate J.*, 3: 311–319 (1986) and Zopf, et al., *Methods Enzymol.*, 50: 171–175 (1978), both of which are incorporated herein by reference. The ratio of protein/carbohydrate is determined by a combination of Lowry protein determination and ribose determination. The ratio is primarily a function of the ratio of carbohydrate to protein in the initial reaction mixture and the type of spacer used. As shown in Example 3, the use of a spacer terminating in an amino group (Compound 16) results in a greater number of oligosaccharides being coupled to the protein than the use of a spacer terminating in an aldehyde group (Compound 14). Table 4 shows the formulas of the final conjugates.

Vaccines

The adhesin-oligosaccharide conjugates, as well as their protein components as previously mentioned, may be used in vaccines against both invasive and non-invasive strains of *H. influenzae.* The conjugate vaccines should have greatest utility against *H. influenzae* type b.

The vaccines comprise an immunologically effective amount of the immunogen in a pharmaceutically acceptable carrier. The combined immunogen and carrier may be an aqueous solution, emulsion, or suspension. An immunologically effective amount is determinable by means known in the art without undue experimentation, given the teachings contained herein. In general, the quantity of immunogen will be between 0.1 and 100 micrograms per dose. The carriers are known to those skilled in the art and include stabilizers, diluents, and buffers. Suitable stabilizers include carbohydrates, such as sorbitol, lactose, manitol, starch, sucrose, dextran, and glucose and proteins, such as albumin or casein. Suitable diluents include saline, Hanks Balanced Salts, and Ringers solution. Suitable buffers include an alkali metal phosphate, an alkali metal carbonate, or an alkaline earth metal carbonate. The vaccine may also contain one or more adjuvants to improve immunogenicity. Suitable adjuvents include aluminum hydroxide, aluminum phosphate, or aluminum oxide or a composition that consists of a mineral oil, such as Marcol 52, or a vegetable oil and one or more emulsifying agents.

The vaccine may also contain other immunogens. Such a cocktail vaccine has the advantage that immunity against several pathogens can be obtained by a single administration. Examples of other immunogens are those used in the known DPT vaccines.

The vaccines of the invention are prepared by techniques known to those skilled in the art, given the teachings contained herein. Generally, the immunogens are mixed with the carrier to form a solution, suspension, or emulsion. One or more of the additives discussed above may be in the carrier or may be added subsequently. The vaccine preparations may be dessicated, for example, by freeze drying for storage purposes. If so, they may be subsequently reconstituted into liquid vaccines by the addition of an appropriate liquid carrier.

The vaccines are administered to humans or other mammals, including rodents and primates. Preferably, they are administered to human children, most preferably children younger than 18 months of age. They can be administered in one or more doses. The vaccines may be administered by known routes of administration for this type of vaccine. The preferred routes are intramuscular or subcutaneous injection. Accordingly, the invention also comprises a method for inducing an immune response to Hi in a mammal in order to protect the mammal against infection by invasive or non-invasive Hi. The method comprises administering an immunologically effective amount of the immunogens of the invention to the host and, preferably, administering the vaccines of the invention to the host.

Reagents

The conjugates, protein/polypeptides, and oligomers of the invention are also useful as reagents for scientific research on the properties of pathogenicity, virulence, and infectivity of Hi, as well as host defense mechanisms. For example, the DNA of the invention can be used in an oligonucleotide probe to identify the DNA of other microorganisms that might encode an adhesin for such organism. The protein of the invention could be used to make a monoclonal antibody that could be used to further purify compositions containing the protein by affinity chromatography. The protein could also be used in standard immunoassays to screen for the presence of antibodies to *H. influenza* in a sample. A composition in accordance with the present invention useful as an investigational reagent contains an amount of conjugate, protein/polypeptide, or oligomer effective to provide the information or analysis sought. The determination of the amount necessary to accomplish a particular research goal depends upon the specific type of investigation involved and is readily within the routine skill of one engaged in such research, once given the teachings contained herein.

It is to be understood that the application of the teachings of the present invention to a specific problem or environment will be within the capabilities of one having ordinary skill in the art in light of the teachings contained herein. Examples of the products of the present invention and processes for their preparation and use appear in the following examples.

EXAMPLE 1

Preparation of Synthetic PRP Oligosaccharide

The preparation of the synthetic PRP oligosaccharides of the invention is illustrated as described herein and as shown in the reaction schemes outlined in Tables 1–3.

Methyl 5-O-allyl-2,3-O-isopropylidene-beta-D-ribofuranoside (Compound 2)

A solution of methyl 2,3-O-isopropylidene-beta-D-ribofuranoside (Compound 1, 50.0 g), N,N-dimethyl formamide (250 ml), and powdered sodium hydroxide (55.0 g) was stirred while allyl bromide (50.0 ml) was added dropwise. After 2 h, the excess allyl bromide was destroyed by addition of methanol (50 ml). After being stirred for another hour, the mixture was partitioned between water and toluene. The organic phase was washed with water, dried with magnesium sulfate, and concentrated. Barium carbonate (250 mg) was added and the oil was distilled at 90°–95° C., 0.75 mm Hg. The yield of Compound 2 was approximately 90%.

5-O-allyl-2,3,4-tri-O-benzyl-D-ribitol (Compound 3)

Methyl 5-O-allyl-2,3-O-isopropylidene-beta-D-ribofuranoside (Compound 2, 1.5 g) in aqueous formic acid (25 ml) was heated on an oil bath at 100° C. for 10 hrs and was then concentrated and coevaporated twice with water. The obtained syrupy material, consisting mainly of 5-O-allyl-D-ribose and residual formic acid, was dissolved in water (25 ml), and the pH was adjusted to 7 with aqueous ammonia. Sodium borohydride (0.5 g) was added, and the mixture was stirred for 3 h, then adjusted to pH 7 with acetic acid, and concentrated. After three coconcentrations with acetic acid-methanol (1:1) and two coconcentrations with methanol, the residue was dissolved in water (50 ml), and the solution was slowly passed through a column of Dowex-50W×2 (H+ form, 50–100 mesh, 2×20 cm) ion exchange resin. The eluate, consisting mainly of 5-O-allyl-D-ribitol, was concentrated, taken up in pyridine, concentrated, and taken up again in pyridine (25 ml). Triphenylmethyl chloride (8.0 g) was added, and the mixture was stirred at room temperature for 16 h, then methanol (2.0 ml) was added. After 15 min, the mixture was partitioned between dichloromethane and water. The organic layer was washed with water, sulfuric acid, and aqueous sodium hydrogen carbonate, dried (magnesium sulfate), and concentrated. The residue was dissolved in N,N-dimethyl formamide (25 ml). The solution was stirred while powdered sodium hydroxide (3.5 g) was added, followed by benzyl chloride (4.40 ml, dropwise). After 2 hours, methanol (5 ml) was added, and after 15 min the mixture was partitioned between toluene and water. The organic layer was washed with water and concentrated. The residue was dissolved in 90% aqueous acetic acid (50 ml) and heated to 100° C. for 2 h, then concentrated and co-concentrated with toluene. The residue was purified by chromatography on silica gel. The compound was eluted with toluene-ethyl acetate 9:1. The yield of syrupy Compound 3 was 48%.

(Compound 4)

Methyl 5-O-benzyl-2,3-O-isopropylidene-beta-D-ribofuranoside

A solution of methyl-2,3-O-isopropylidene-beta-D ribofuranoside (Compound 1, 50 g), N,N-dimethyl formamide (250 ml), and powdered sodium hydroxide (50 g) was stirred while benzyl chloride (64 ml) was added dropwise. After 2 h, the excess of benzyl chloride was destroyed by addition of methanol (50 ml). After being stirred for another hour, the mixture was partitioned between water and toluene. The organic phase was washed with water, dried with magnesium sulfate, and concentrated. Barium carbonate (250 mg) was added and the oil was distilled at 115°–120° C., 0.4 mm Hg. The yield of Compound 4 was approximately 90%.

(Compound 5)

Methyl 5-O-benzyl-2,3-di-O-benzoyl-beta-D-ribofuranoside

A solution of methyl 5-O-benzyl-2,3-O-isopropylidene-beta-D-ribofuranoside (Compound 4, 23 g) in 95:5 formic acid-water (200 ml) was kept at room temperature for 30 min, then cooled in ice. The cooled solution was poured into a vigorously stirred mixture of crushed ice, aqueous sodium hydroxide (240 g in 2000 ml), and dichloromethane (1000 ml). The mixture was shaken well in a separatory funnel, the organic layer was separated, and the aqueous layer was extracted four times with 500 ml portions of dichloromethane. The combined organic extracts, containing mainly methyl 5-O-benzyl-beta-D-ribofuranoside were concentrated. Dry pyridine (50 ml) was added, the mixture was concentrated, then dry pyridine (150 ml) was added again. The mixture was cooled in ice while benzoyl chloride (34 ml) was added dropwise. The mixture was further stirred at room temperature overnight, then water (2 ml) was added to destroy excess benzoyl chloride. The mixture was then partitioned between water (1000 ml) and dichloromethane (500 ml). The organic layer was washed with 2M aqueous sulfuric acid, then with 1M aqueous sodium hydrogen carbonate. Concentration yielded a syrup, which was purified on a column of silica gel. The fractions containing pure material were pooled and concentrated. The material could be crystallized from methanol in the cold, mp 68°–69° C. The yield of Compound 5 was 22–41%. The chromatography also gave some starting material (Compound 4) in pure form (5–20%).

3-O-allyl-5-O-benzyl-1,2-O-methoxybenzylidene-alpha-D-ribofuranose (6)

A solution of hydrogen bromide in dichloromethane was prepared by mixing dichloromethane (150 ml), methanol (3.0 ml), and acetyl bromide (6.0 ml). Then methyl 2,3-di-O-benzoyl-5-O-benzyl-beta-D-ribofuranoside (Compound 5, 4.62 g) was added, and the mixture was stirred at room temperature for 30 min., after which the mixture, containing mainly 2,3-di-O-benzoyl-5-O-benzyl-alpha-D-ribofuranosyl bromide, was cooled in ice while collidine (25 ml) was added dropwise with stirring, followed by methanol (10 ml). The mixture was further stirred for 3h at room temperature, then washed with water, concentrated, and co-concentrated with methanol. The residue, containing mainly 3-O-benzoyl-5-O-benzyl-1,2-O-methoxybenzylidene-alpha-D-ribofuranose, was dissolved in methanol (50 ml), and a solution of sodium methoxide in methanol (0.5M, 20 ml) was added. After 2 h at room temperature, the mixture was neutralized by addition of $CO_2$(s), then concentrated and co-concentrated once with N,N-dimethylformamide. The residue was dissolved in N,N-dimethylformamide (50 ml) and stirred at room temperature while powdered sodium hydroxide (3.0 g) was added, followed by allyl bromide (3.0 ml). After 1 h, the mixture was partitioned between water and toluene, the organic layer was washed with water, and concentrated. The residue was purified by chromatography on silica gel using toluene-ethyl acetate-pyridine (90:10:1) as the eluant. The appropriate fractions were pooled and concentrated to give Compound 6 (1.90 g, 48%) as a colorless syrup.

2,3,4-tri-O-benzyl-1-O-(2,5-di-O-benzyl-beta-D-ribofuranosyl)-5-O-monomethoxytrityl-D-ribitol (Compound 7)

Glycosidation Method A

Compound 6 (4.0 g) was dissolved in trimethylsilyl chloride (20 ml). After 20 min. at room temperature, the solution was concentrated, then co-concentrated with dry dichloromethane. The residue was dissolved in dry dichloromethane (25 ml) containing powdered 4A molecular sieves (5.0 g) and Compound 3 (4.6 g). The mixture was stirred at room temperature overnight. The mixture was filtered and concentrated. The residue was purified by column. chromatography (toluene-ethyl acetate 15:1 as eluant) and then taken up in 0.04M methanolic sodium methoxide (50 ml). After 1 hr at room temperature, the mixture was neutralized by addition of $CO_2$(s), then concentrated and co-concentrated once with N,N-dimethylformamide. The residue was dissolved in N,N-dimethylformamide (50 ml) and stirred at room temperature while powdered sodium hydroxide (3.0 g) was added, followed by benzyl chloride (3.0 ml). After 1 h, the mixture was partitioned between water and toluene, and the organic layer was washed with water and concentrated. The residue was purified by chromatography on a short column of silica gel using toluene-ethyl acetate (9:1) as eluant. The fractions containing 5-O-allyl-2,3,4-tri-O-benzyl-1-O-(3-O-allyl-2,5-di-O-benzyl-beta-D-ribofuranosyl)-D-ribitol were pooled and concentrated. The residue was dissolved in 30:12:4 ethanol-toluene-water (75 ml), and the solution was refluxed in the presence of tris(triphenylphosphine)rhodium(I)chloride (200 mg) until thin-layer chromatography showed complete conversion. The mixture was concentrated and taken up in acetic acid-water (30 ml, 9:1 by volume) and the mixture was heated to 80° C. for 1 hour, concentrated and the residue was partitioned between diethyl ether and water, dried, and concentrated. The residue, containing mainly 2,3,4-tri-O-benzyl-1-O-(2,5-di-O-benzyl-beta-D-ribofuranosyl)-D-ribitol, was taken up in dry pyridine (50 ml), and monomethoxytrityl chloride (3.5 g) was added. The mixture was stirred overnight, then methanol was added to destroy the excess chloride. After 30 min, the mixture was partitioned between dichloromethane and water, then washed with aqueous sulfuric acid and aqueous sodium bicarbonate, dried, and concentrated. The residue was purified by chromatography on a column of silica gel using toluene-ethyl acetate (9:1, containing 1% pyridine) as eluant. The appropriate fractions were pooled and concentrated to give Compound 7 (4.9 g, 50%, calculated from 6) as a colorless syrup.

Glycosidation Method B

Compounds 3 (4.6 g) and 6 (4.0 g) were dissolved in dry nitromethane (60 ml). Methanol was removed by continuous distillation at constant volume with continuous addition of nitromethane until thin-layer chromatography showed complete transesterification of Compound 6. Mercury (II) bromide (500 mg) was added, and solvent was distilled off at constant volume with continuous addition of nitromethane until thin-layer chromatography showed the formation of a new product. The mixture was purified by chromatography and treated further as described under method A above.

2,3,4-tri-O-benzyl-1-O-(2,5-di-O-benzyl-beta-D-ribofuranosyl)-5-O-monomethoxytrityl-D-ribitol 3-H-phosphonate (Compound 8)

Compound 7 (4.9 g) was taken up in dry pyridine, and concentrated to dryness, then taken up in pyridine (20 ml) and added to a solution of phosphonic acid (4.1 g) in pyridine (20 ml). 5,5-dimethyl-2-oxo-2-chloro-1,3,2-dioxaphosphorinane (5.0 g) was added. When thin-layer chromatography showed complete conversion, 1M aqueous triethylammonium bicarbonate (5 ml) was added, and the mixture was partitioned between dichloromethane (200 ml) and 0.5M aqueous triethylammonium bicarbonate (130 ml). The organic layer was concentrated, and the residue was purified by chromatography on a short column of silica gel using a stepwise gradient of methanol in dichloromethane (0–20%, containing 1% pyridine) as eluant. The yield of amorphous Compound 8 was 80–90%.

2,2-Diethoxyethyl 2,5-di-O-benzyl-beta-D-ribofuranoside (Compound 9, p=1, $R^3$=ethyl)

A mixture of Compound 6 (2.0 g) and trimethylsilyl chloride (15 ml) was kept at room temperature for 20 min., then concentrated, and co-concentrated with dry dichloromethane. The residue was mixed with glycolaldehyde diethylacetal (1.0 g), powdered 4 A molecular sieves (3.0 g), and dry dichloromethane (15 ml) and was stirred at room temperature overnight, then filtered and concentrated. The residue was taken up in 0.04M methanolic sodium methoxide (25 ml). After 1 hr. at room temperature, the mixture was neutralized by addition of $CO_2$(s) then concentrated and coconcentrated once with N,N-dimethylformamide. The residue was dissolved in N,N-dimethylformamide (20 ml) and stirred at room temperature while powdered sodium hydroxide (3.0 g) was added, followed by benzyl chloride (3.0 ml). When TLC indicated complete conversion, methanol (2 ml) was added, and after 15 min. the mixture was partitioned between water and toluene, the organic layer was washed with water and concentrated. The residue was purified by chromatography on a short column of silica gel using toluene-ethyl acetate (8:2) as eluant. The appropriate fractions were collected and concentrated, them taken up in 30:12:4 ethanol-toluene-water (50 ml), and the solution was refluxed in the presence of tris(triphenylphosphine)rhodium (I)chloride (100 mg) until thin-layer chromatography showed complete conversion. The mixture was then diluted with dichloromethane, washed with saturated aqueous potassium chloride, and concentrated. The residue was dissolved in 10:1 acetone-water (20 ml), and mercuric oxide (2.0 g) followed by mercuric chloride (2.0 g) was added. After stirring at room temperature for 30 min., the solids were removed by filtration, and the filtrate was partitioned between diethyl ether and water, washed with aqueous potassium iodide, dried, and concentrated. Purification on a short silica gel column, using toluene-ethyl acetate (8:2) as eluant, gave syrupy Compound 9. The yield was 60–65%.

2-[2-(benzyloxycarbonylamido)ethoxy]ethyl 2,5-di-O-benzyl-beta-D-ribofuranoside (Compound 11, p=1, $R^4$=NHCOOBn)

A mixture of Compound 6 (2.0 g) and trimethylsilyl chloride (15 ml) was kept at room temperature for 20 min., then concentrated, and co-concentrated with dry dichloromethane. The residue was mixed with 2-[2-(benzyloxycarbonylamido)ethoxy]ethanol (1.5 g), powdered 4 A molecular sieves (3.0 g), and dry dichloromethane (15 ml) and was stirred at room temperature overnight, then filtered and concentrated. The residue was taken up in 0.04M methanolic sodium methoxide (25 ml). After 1 hr. at room temperature, the mixture was neutralized by addition of $CO_2$(s), then concentrated and co-concentrated once with N,N-dimethylformamide. The residue was dissolved in N,N-dimethylformamide (20 ml) and stirred at room temperature while freshly prepared silver oxide (3.0 g) was added, followed by benzyl bromide (3.0 ml). When thin layer chromatography indicated complete conversion, the mixture was filtered. The filtrate was partitioned between water and toluene, the organic layer was washed with water and aqueous sodium thiosulfate, and concentrated. The residue was purified by chromatography on a short column of silica gel using toluene-ethyl acetate (8:2) as eluant. The appropriate fractions were collected and concentrated, then treated with selenium dioxide (570 mg) and acetic acid (0.4 ml) in dioxane (14 ml) at reflux for 40 min. The mixture was then filtered through Celite. The yield of syrupy Compound 11 after chromatographic purification was 50%.

2-(2-Azidoethoxy)ethyl 2,5-di-O-benzyl-beta-D-ribofuranoside (Compound 11, p=1, $R^4$=$N_3$)

A mixture of Compound 6 (2.0 g) and trimethylsilyl chloride (15 ml) was kept at room temperature for 20 min., then concentrated, and co-concentrated with dry dichloromethane. The residue was mixed with 2-(2-azidoethoxy) ethanol (2.0 g), powdered 4 A molecular sieves (3.0 g), and dry dichloromethane (15 ml) and was stirred at room temperature overnight, then filtered and concentrated. The residue was taken up in 0.04M methanolic sodium methoxide (25 ml). After 1 hr. at room temperature, the mixture was neutralized by addition of $CO_2$(s), then concentrated and co-concentrated once with N,N-dimethylformamide. The residue was dissolved in N,N-dimethylformamide (20 ml) and stirred at room temperature while powdered sodium hydroxide (3.0 g) was added, followed by benzyl chloride (3.0 ml). When thin layer chromatography indicated complete conversion, methanol (2 ml) was added, and after 15 min. the mixture was partitioned between water and toluene, the organic layer was washed with water and concentrated. The residue was purified by chromatography on a short column of silica gel using toluene-ethyl acetate (8:2) as eluant. The appropriate fractions were collected and concentrated, then treated with, acetic acid (0.4 ml), dioxane (14 ml) and selenium dioxide (0.57 g) at reflux for 40 min. The mixture was filtered and concentrated. The yield of syrupy Compound 11 after chromatograhic purification was 50%.

2,2-Diethoxyethyl 2,5-di-O-benzyl-beta-D-ribofuranoside 3-H-phosphonate (Compound 10, p=1, $R^3$=ethyl)

Compound 9 was treated with phosphonic acid and condensing reagent essentially as described for the preparation of compound 8 to give amorphous Compound 10 (67%).

2-[2-(benzyloxycarbonylamido)ethoxy]ethyl 2,5-di-O-benzyl-beta-D-ribofuranoside 3-H-phosphonate (Compound 12, p=1, $R^4$=NHCOOBn)

Compound 11 was treated with phosphonic acid and condensing reagent essentially as described for the preparation of Compound 8 to give amorphous Compound 12 (75%).

2-(2-Azidoethoxy)ethyl 2,5-di-O-benzyl-beta-D-ribofuranoside 3-H-phosphonate (Compound 12, p=1, $R^4$=$N_3$)

Compound 11 was treated with phosphonic acid and condensing reagent essentially as described for the preparation of Compound 8 to give amorphous Compound 12 (70%).

Solid phase synthesis: chain initiation

1. Preparation of the 3-succinate of Compound 7

To a solution of Compound 7 (4 mmol) in dry pyridine (25 ml) containing 4-dimethylaminopyridine (1 mmol) was added succinic anhydride (10 mmol). After stirring overnight water (0.5 ml) was added. After 3 hrs. the mixture was partitioned between 1:1 toluene-ethyl acetate and aqueous phosphate buffer (pH 6.5). The organic lager was washed with buffer, and concentrated. The obtained 3-succinate of 7 was dried in vacuum over phosphorous pentoxide.

2. Coupling of the 3-succinate to the solid phase

The succinate obtained above (10 equivalents over the resin amino group content) was dissolved in dichloromethane (5 ml/g) and mixed with a solution of dicyclohexylcarbodiimide (5 equivalents over the resin amino group content) in a small volume of dichloromethane. The mixture was stirred for 15 min. at room temperature, then concentrated. The residue was dissolved in N,N-dimethylformamide (5 ml/g) and the solution was filtered, then added to Merrifield-type aminomethyl resin (prewashed with N,N-dimethylformamide). After 6 h, the resin was washed with N,N-dimethylformamide, then with pyridine. The resin was treated with 9:1 pyridine-acetic anhydride for 2 hr., washed with pyridine, then washed with dichloromethane. The degree of functionalization was determined by treating a dried and weighed amount of resin with 0.5% trifluoroacetic acid in 1,2-dichloroethane, and estimating the trityl cation content in the supernatant by spectrophotometry (495 nm). A typical value was 0.5 mmol/g.

Solid phase synthesis: chain elongation cycle

The solid-phase synthetic operations were carried out in a semi-automated apparatus, consisting of a reaction vessel with a glass filter bottom, agitation device (small scale batches were agitated by pressing dry nitrogen through the bottom filter), liquid outlet (bottom), and liquid inlet (top). Liquid was removed from the vessel through the bottom filter by suction, and added at the top by pressing with nitrogen from other vessels through teflon tubing.

1. Trityl deprotection

The resin was treated with a 0.5% solution of trifluoroacetic acid in dichloromethane until no more trityl cation was released (as determined spectrophotometrically), then the resin was washed with dichloromethane, followed by 4:1 dichloromethane-pyridine.

2. Coupling

Pivaloyl chloride (4 equivalents over the resin hydroxyl groups) in dichloromethane (2ml/mmol. chloride) was added to a solution of compound 8 (4 equivalents) in 4:1 dichloromethane-pyridine (8ml/mmol. chloride). After 2 min., the mixture was added to the resin. Agitation was continued for 10 min, then the resin was washed with, successively, pyridine and 4:1 dichloromethane pyridine and dichloromethane. The yield in each coupling step was 97%–99%, as determined spectrophotometrically by the amount of the released trityl cation in the deprotection step.

Chain Termination

Detritylated resin was treated as under (2) but with compound 9 or 11 instead of 8.

Oxidation

The resin was treated with a freshly prepared 1% solution of iodine in 98% aqueous pyridine for 30 min., then washed with, successively, pyridine and dichloromethane.

Removal from resin

The resin was treated with sodium methoxide 1:1 dioxane-methanol (0.05M) for 16 hours at room temperature, acetic acid was added, and the mixture was then filtered and the filtrate was concentrated. The residue, according to NMR analysis, contained compound 13 (if 10 was used for chain termination) or 15 (if 12 was used for chain termination), together with impurities.

Deprotection

1. Conversion of Compound 13 to Compound 14

The material that was removed from the resin as described above was dissolved in 1:2:2 ethylacctate-ethanol-water (0.1 ml/mg material) containing acetic acid (0.3%), and 10% Pd/C (0.5–2 mg/mg material) was added. The mixture was hydrogenated at 60° C. and atmospheric pressure overnight, then filtered, adjusted to pH 7, and concentrated. The residue was partitioned between diethyl ether and water. The aqueous layer was separated and concentrated. The residue was taken up in 50% aqueous trifluoroacetic acid at 0° C. After 4 h, the mixture was neutralized at 0° C. with ammonia to pH 7, then the mixture was concentrated to a volume of approximately 10 mg/ml, and applied to a column of Fractogel TSK HW-50, packed and eluted with 10 mM ammonium bicarbonate buffer, pH6.2. The appropriate fractions were collected, concentrated, and redissolved in water (0.1 ml/mg material). This solution was slowly passed through a column of Dowex-50×8 (Na form, packed and eluted with water). The appropriate fractions were collected and lyophilized. NMR spectroscopy in $D_2O$ solution showed, inter alia, signals from the anomeric protons in the region 4.9–5.1 ppm and signals from the spacer unit (aldehyde proton, dihydrate form) at 5.1–5.2 ppm. The amount of successful coupling cycles (that is, the value of n in formula for Compound 14) was verified by integration over the anomeric signals and the spacer signals, respectively.

2. Conversion of Compound 15 to Compound 16

The material that was removed from the resin was treated essentially as described above for conversion of Compound 13 to 14, except that the trifluoroacetic acid treatment was omitted. NMR spectroscopy in $D_2O$ solution of the lyophilized product showed, inter alia, signals from the anomeric protons in the region 4.9–5.1 ppm and signals from the spacer unit ($CH_2N$ triplet) at 3.2 ppm. The amount of successful coupling cycles (that is, the value of n in the formula for Compound 16) was verified by integration over the anomeric signals and the spacer signals, respectively. The purification of 14 and 16 could also be effected by preparative HPLC on Nucleosil C-18, using 0.1M aqueous triethylammonium acetate (pH 5.3) with 2.5% acetonitrite as eluant.

EXAMPLE 2

Purification of an Hib Adhesin

Bacteria were grown 24 h in defined media and labeled metabolically with $^{35}$S-methionine. Cells were harvested and washed by centrifugation three times in saline and suspended in approximately 20 ml of 10 mM Hepes buffer, pH 7.4, and chilled on ice. The bacterial suspension was then sonicated on ice 6 times for 30 seconds each at a setting of 4 on a Bronson Sonicator. The sonic extract was centrifuged at 10,000×g for 10 min. at 4° C., and the resulting outer membrane protein (OMP) pellet was stored until use in Hepes buffer containing protease inhibitors (PIC I & PIC II).

OMPs were next centrifuged at 100,000×g for 30 min. at 4° C. and the resulting pellet was suspended in 4 ml of 10 mM Hepes, pH 8.0, containing 1.3% octylglucopyranoside (Sigma), sonicated 5 min., and incubated at room temperature for 30 min. The resulting solubilized OMPs were centrifuged again at 100,000×g for 30 min. at 4° C., and the supernatant containing partially purified adhesin was decanted and saved.

The adhesin was purified by a receptor-affinity solid phase procedure as follows. The supernatant was diluted 1/10 in 50 mMTris-HCl, pH 7.8, containing 150 mM NaCL and 1% bovine serum albumin (BSA) and incubated in receptor-coated microtiter wells (0.8 micrograms of gangliotetraosylceramide/well) which had been previously blocked with BSA. Control wells lacking receptor were also used. After a 2 h incubation at room temperature, wells were washed 4 times with cold saline. The receptor-bound adhesin was eluted by incubating the wells for 30 min. at 37° C. with 0.05 ml of 10 mM Tris-HCl, pH 7.8, containing 0.1% SDS which had been previously heated to 60° C. The SDS elution buffer was removed from the wells and analyzed for protein by SDS-PAGE and autoradiography.

Alternatively, the adhesin can be purified by using an affinity chromatography column where the lipid receptor is immobilized onto an appropriate gel solid support. The sonic extract is loaded on the top of the gel and the column is washed to remove unbound material. The adhesin is then eluted with SDS elution buffer or a chaotropic agent, such as NaCl or KSCN, and dialyzed and analyzed by SDS-PAGE and autoradiography.

The molecular weight of the purified adhesin protein was determined by SDS-polyacrylamide gel electrophoresis. FIG. 1 shows the sample analysis in the following lanes: 1, total outer membrane protein preparation from *Haemophilus influenzae* type b stained with Coomassie blue; 2, autoradiography of $^{35}$S-labeled total outer membrane proteins; 3, autoradiography of 35S-labeled adhesin protein eluted from immobilized receptor asialo-$GM_1$; 4, autoradiography of material eluted from immobilized globoside, a nonsense glycolipid. Arrow indicates the adhesin migrating between P1 and P2 with a molecular weight of about 41 kD.

EXAMPLE 3

Neutralization of Adhesin Binding to Receptor

BALB C mice were injected IP with 10 micrograms of partially purified adhesin protein (Hib OMPs) in complete Freunds adjuvant (1:1). After one month, the mice were boosted with a second IP injection (10 micrograms of protein) using incomplete Freunds adjuvant followed by a third injection 10 days later.

Figure 2:
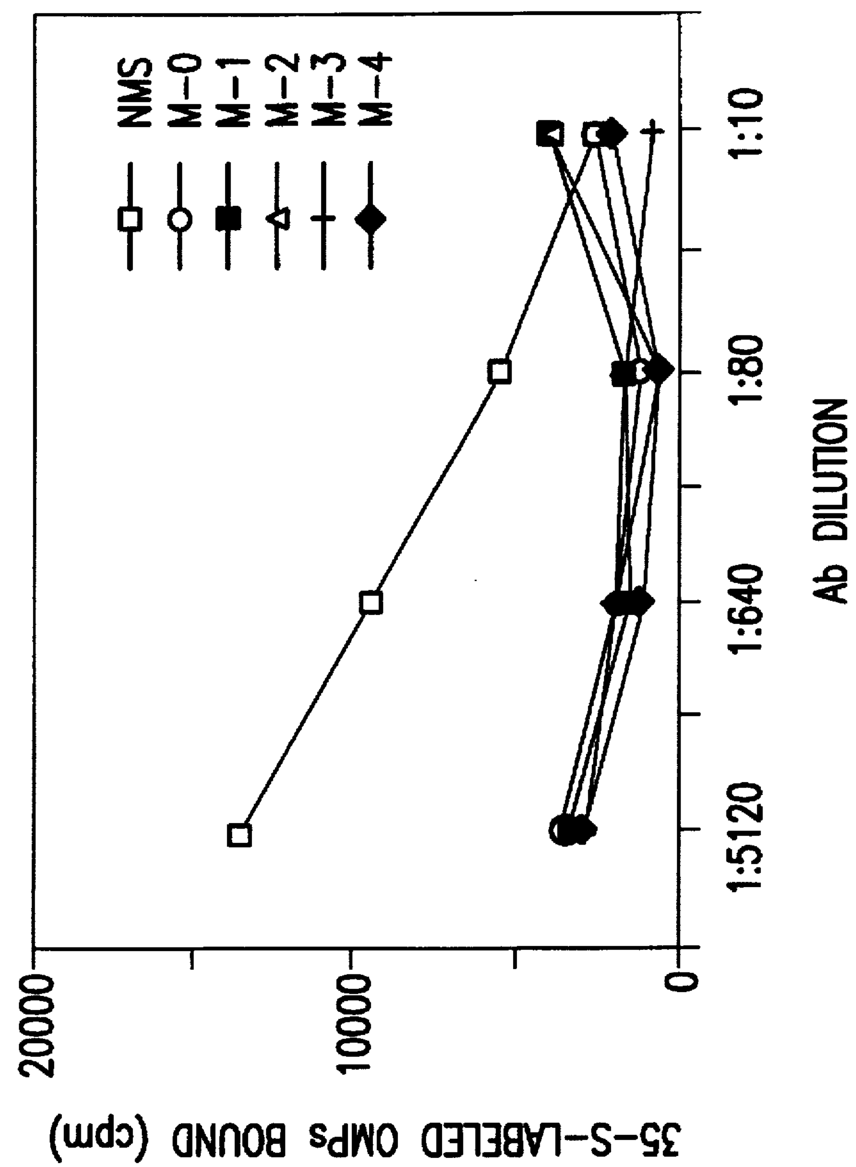
FIG. 2 shows the neutralization of Haemophilus adhesin to the glycolipid receptor asialo-$GM_1$. [$^{35}S$]methionine-labeled membranes from *Haemophilus influenza* type b were incubated with serial dilutions of mouse sera and then allowed to bind to receptor (0.5 microgram/well). The mouse sera used was obtained from 5 mice, designated M-0 through M5, which had been immunized with Haemophilus membranes. The sera from an unchallenged mouse (NMS) was used as a negative control.

Antiserum was then tested for neutralizing activity against $^{35}$S-labeled Hib adhesin in a receptor binding assay. In this case, antiserum and normal mouse serum at various dilutions were incubated with $^{35}$S-labeled Hib adhesin protein for one hour at room temperature and then added to microtiter wells coated with asialo-GM1 or globoside as a negative control. After incubation of the microtiter plates for 2 hours at room temperature, the microtiter wells were washed, cut from the plates and radioactivity was quantified using a Beta-scintillation counter. The results are shown in FIG. 2. The results show that the adhesin is immunogenic and that antibodies to the adhesin effectively neutralize the adhesin's receptor binding activity.

EXAMPLE 4

Identification and Cloning of an *Haemophilus Influenza* Adhesin

1. Membrane proteins binding to receptor. Membrane proteins were prepared as follows. *Haemophilus influenzae* type b (ATCC 9795) were grown to stationary phase, pelleted, resuspended in saline buffer, and sonically disrupted. This material was then centrifuged at 12,000×g for 15 min, and the supernatant was centrifuged at 100,000×g for 1 h. The resultant pellet contained Haemophilus membranes, which were resuspended in saline and tested for adhesin activity as described in Krivan, et al. *Proc. Natl. Acad. Sci. USA*, 85: 6157–6161 (1988), incorporated herein by reference. Briefly, membranes were prepared from [$^{35}$S] methionine metabolically-labeled cells (1 micro-Ci/ml of media). Glycolipids were resuspended in chloroform:methanol (1:1, vol:vol) and serially diluted into 96-well microtiter plates. These plates were allowed to dry, washed 5 times with Tris/BSA (25 mMTris, pH7.5, 1% bovine serum albumin), then $2\times10^6$ CPM of labeled membranes were added to each well and incubated at room temperature for 2 h. The plates were then washed with Tris/BSA 5 times, and the individual wells cut out and counted on a scintillation counter to determine the amount of CPM bound to each well. This showed that Hi membranes bound similar to Hi whole cells.

Figure 3:
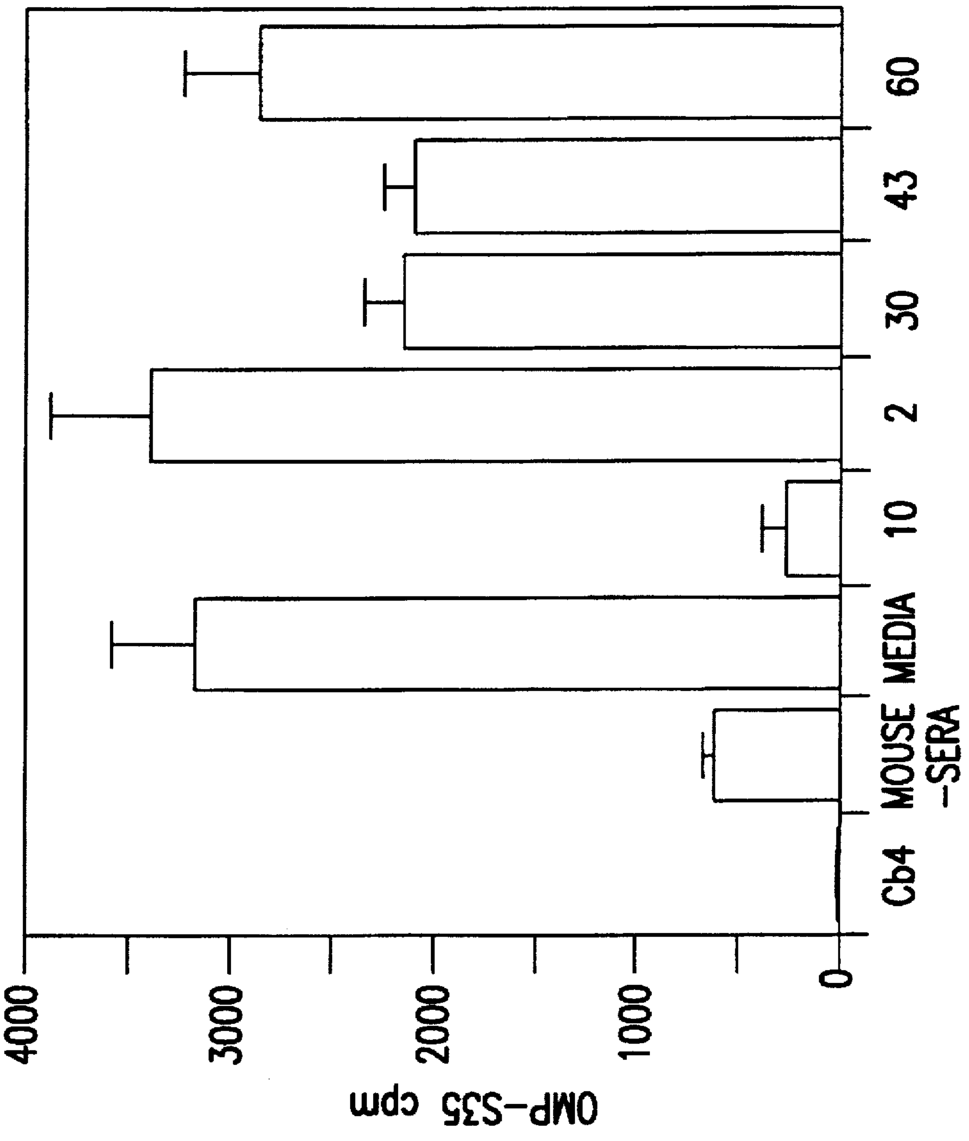
FIG. 3 shows inhibition of Haemophilus membrane binding to asialo-$GM_1$ with selected monoclonal antibodies. [$^{35}S$]methionine-labeled membranes from Haemophilus were incubated with supernatants of hybridoma cultures and then allowed to bind to receptor (0.5 microgram/well). A negative receptor control of $Gb_4$ indicates the specificity of the receptor-ligand interaction. Mouse sera (M-2) (1:500 dilution) used in FIG. 2 shows strong, positive inhibition. Media shows no inhibition of binding by membranes to asialo-$GM_1$. Two classes of positively inhibiting hybridomas were found. Hib 10 shows total inhibition of binding. Hib 30 and Hib 43 show partial (about 35%) inhibition. Most hybridoma cultures, such as Hib 2, showed no inhibition. All hybridoma cultures tested for binding reacted positively with membranes in an ELISA. Error bars are included to demonstrate the variability between duplicate wells.

2. Production of monoclonal antibodies that inhibit adhesion of Haemophilus. Balb/c mice were immunized with membranes from *Haemophilus influenzae* type b (ATCC 9795), and their sera was tested for the development of antibody that inhibited membranes from binding to receptor (FIG. 2). Spleens from these mice were used to isolate splenocytes for fusion with SP2/o-AG14 (ATCC CRL 8287) mouse myeloma cells according to Harlow, et al., *Antibodies: A Laboratory Manual* (Cold Spring Harbor Laboratory, Cold Spring Harbor, N.Y.) (1988), incorporated herein by reference. Seven hundred and fifty positive fusion hybridoma cultures from four separate fusions were screened for the production of antibody that reacted on ELISA with membranes. The ELISA was performed as follows. Membranes containing 1 microgram of protein were used to coat 96-well microtiter plates. The coated wells were washed with PBS (phosphate buffered saline, 10 mM sodium phosphate, pH 7.5, 167 mM sodium chloride), then incubated with 100 microliters of hybridoma culture supernatant. The wells were washed, incubated with 100 microliters of secondary goat anti-mouse antibody conjugated with horseradish peroxidase for 1 h, then bound antibody was detected colorimetrically (Biorad). Seventy-five membrane-reactive hybridoma cultures were then tested for the ability to inhibit membrane binding (FIG. 3). Hybridoma culture supernatants were incubated with $4\times10^6$ CPM of [$^{35}$S] methionine labeled membranes for 1 h at room temperature. This mixture was then added to serial dilutions of receptor bound passively to 96-well microtiter plates and assayed for binding. Two classes of inhibiting antibodies were identified. One class, such as the antibodies designated Hib10, completely inhibited binding and were subsequently shown to react with the lipooligosaccharide component of these membranes. The second class of antibodies, such as those designated Hib30 and Hib43, partially inhibited binding.

Figure 4:
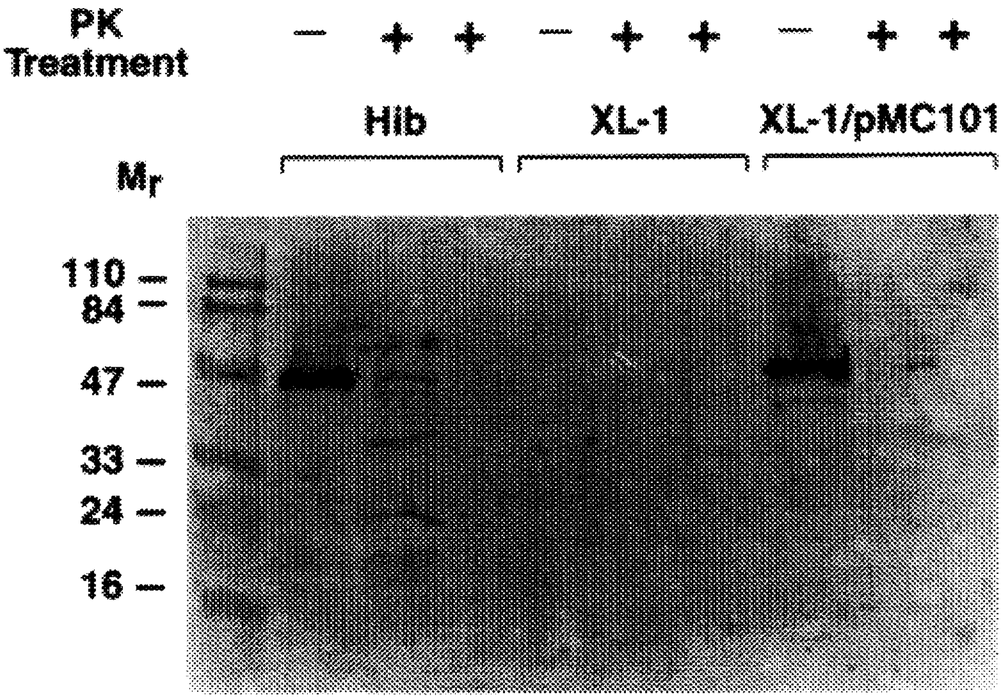
FIG. 4 shows the identification and characterization of the 47 kDa Haemophilus adhesin. The monclonal antibody which partially inhibited membrane binding, Hib 43, was reacted on Western blot to identify the molecular weight of the protein it recognizes. Whole cells were run after no proteinase K treatment or either treatment with proteinase K prior to lysis in sample buffer or treatment with proteinase K after lysis in sample buffer (reading from left to right). Non-treatment identifies the 47 kDa protein; treatment of whole cells by proteinase K prior to lysis indicates the sensitivity of the protein to this protease in its native location; and treatment after lysis by proteinase K demonstrates the general sensitivity to this protease after disruption from that native location. The *Escherichia coli* XL-1, transformed with pMC101, expresses the 47 kDa Haemophilus protein, which reacts with Hib 43. The 47 kDa protein was also sensitive to proteinase K treatment of XL-1/pMC101 whole cells. These data suggest a surface location for this protein in both hosts.

3. Identification of the putative adhesin. The hybridoma cultures which produced antibodies that partially inhibited binding were cloned by limiting dilution to obtain stable cell lines according to Harlow, E. and R. Lane (1988) "Antibodies: A Laboratory Manual," pp. 139–244, Cold Spring Harbor, N.Y., incorporated herein by reference. Large amounts of antibody were produced in the ascitis fluid of Balb/c mice, and the class of each antibody was determined according to Harlow et al. The antibodies were then used on Western blot of Haemophilus membranes and whole cells to identify a potential protein adhesin according to Harlow et al. All of these antibodies recognized an approximate 47 kDa protein, Hin47, by this technique (FIG. 4). Western blot analysis with these antibodies according to Harlow et al. allowed further characterization of this protein. Several lines of evidence suggested that this protein is located on the surface of Haemophilus, as would be expected for a functional adhesin. First, the ability of whole cells to bind the receptor was inhibited by these antibodies in an assay as described above for membrane binding inhibition but using radiolabeled whole cells ($4\times10^6$ CPM/well). Second, the Hin47, a immunoreactive protein, was degraded when whole cells were treated with proteinase K (FIG. 4). Briefly, whole cells were grown to stationary phase, pelleted by centrifugation (12,000×g), and resuspended in PBS. Serial dilutions of proteinase K were added to the cells and incubated for 1 h. Cells were then mixed with SDS-PAGE sample buffer according to Laemmll, *Nature* (*London*), 227:680–685 (1970) (incorporated herein by reference), boiled, and separated on SDS-PAGE. This gel was then Western blotted to detect the presence of an immunoreactive Hin47 protein. Third, iodinated whole cells contained a radiolabeled Hin47 protein that could be immunoprecipitated from solubilized proteins by the anti-adhesin antibodies. Briefly, whole Haemophilus were grown to stationary phase and pelleted by centrifugation. Cells were resuspended in PBS and iodinated with Iodogen (Pierce) according to the manufacturer's recommendation. Cells were then solubilized in radioimmune precipitation buffer (RIPA buffer, 20 mM Tris, pH 7.4, 150 mM NaCl, 1 mM EDTA, 1% Nonidet P-40, 1% deoxcholate, 0.1% SDS, 1 mM PMSF), and then incubated with Gammabind beads (Pharmacia) overnight at 4° C. The beads were then pelleted by centrifugation (2000×g, 5 min), washed 5 times with PBS containing 0.05% Tween-20, and resuspended in SDS-PAGE sample buffer. This sample was then separated by SDS-PAGE, and the gel was dried and autoradiographed. This showed the Hin47 protein was accessible to iodination. Fourth, whole cells and membranes that were extracted repeatedly with 1% Triton X-100 lost this Hin47 immunoreactive protein. This was performed by taking whole cells or membranes and mixing them with the detergent, pelleting the material by centrifugation (12,000×g for membranes and 2000×g for whole cells), and taking the supernatant. This material (pellet and supernatant) was separated by SDS-PAGE gel, Western blotted, and the presence of Hin47 protein detected with Hib 47 antibody in the soluble fraction (supernant).

Figure 5:
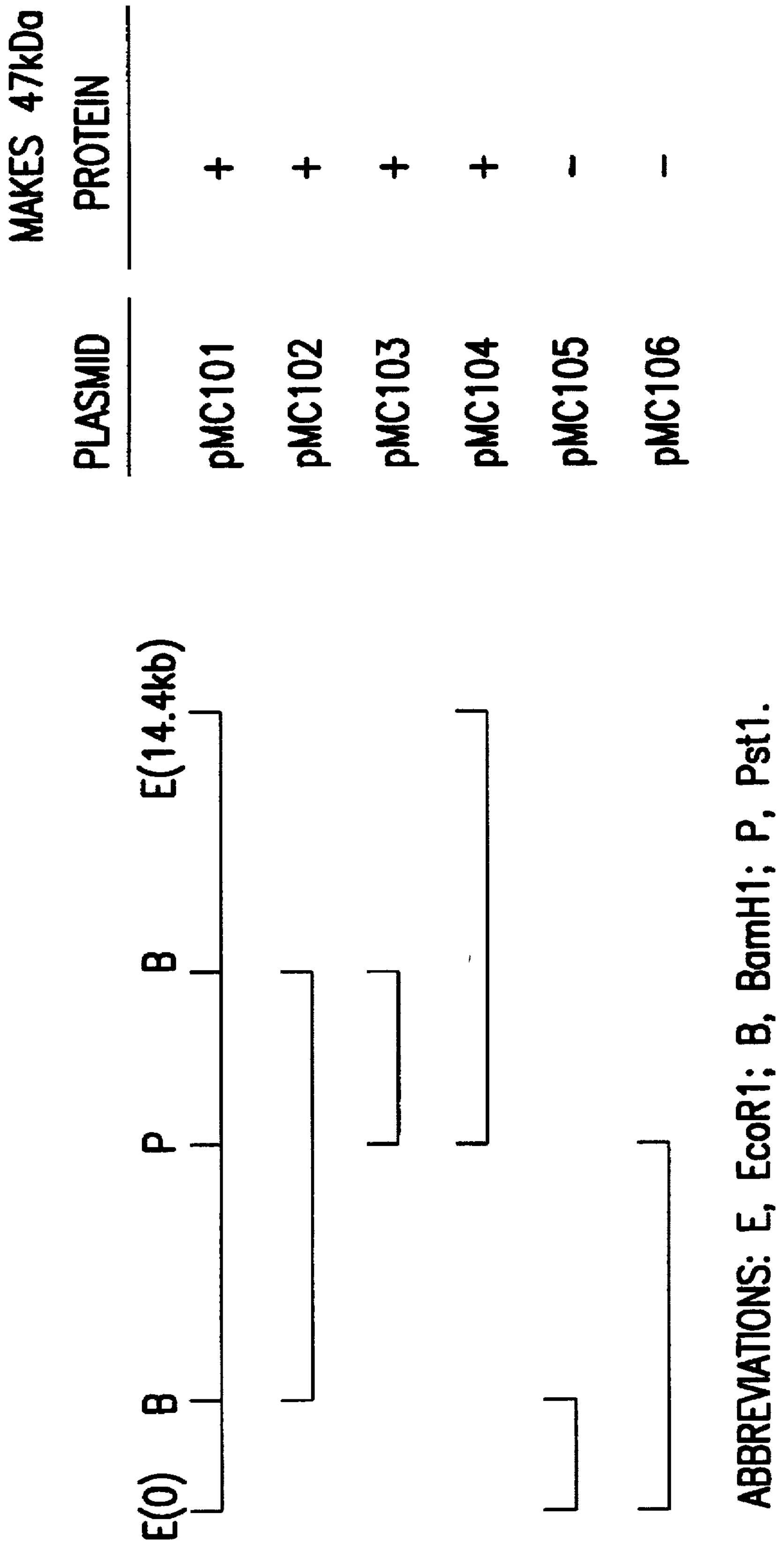
FIG. 5 shows a restriction map of the region in *Haemophilus influenza* type b that encodes the 47 kDa adhesin. A 10.5 kbp Eco R1 fragment that produces the 47 kDa protein which reacts with Hib 43 monclonal antibody was cloned from an Haemophilus lambda ZAPII genebank. The helper phage R408 was used to induce a plasmid containing this insert in the vector pSK(−).
Figure 6:
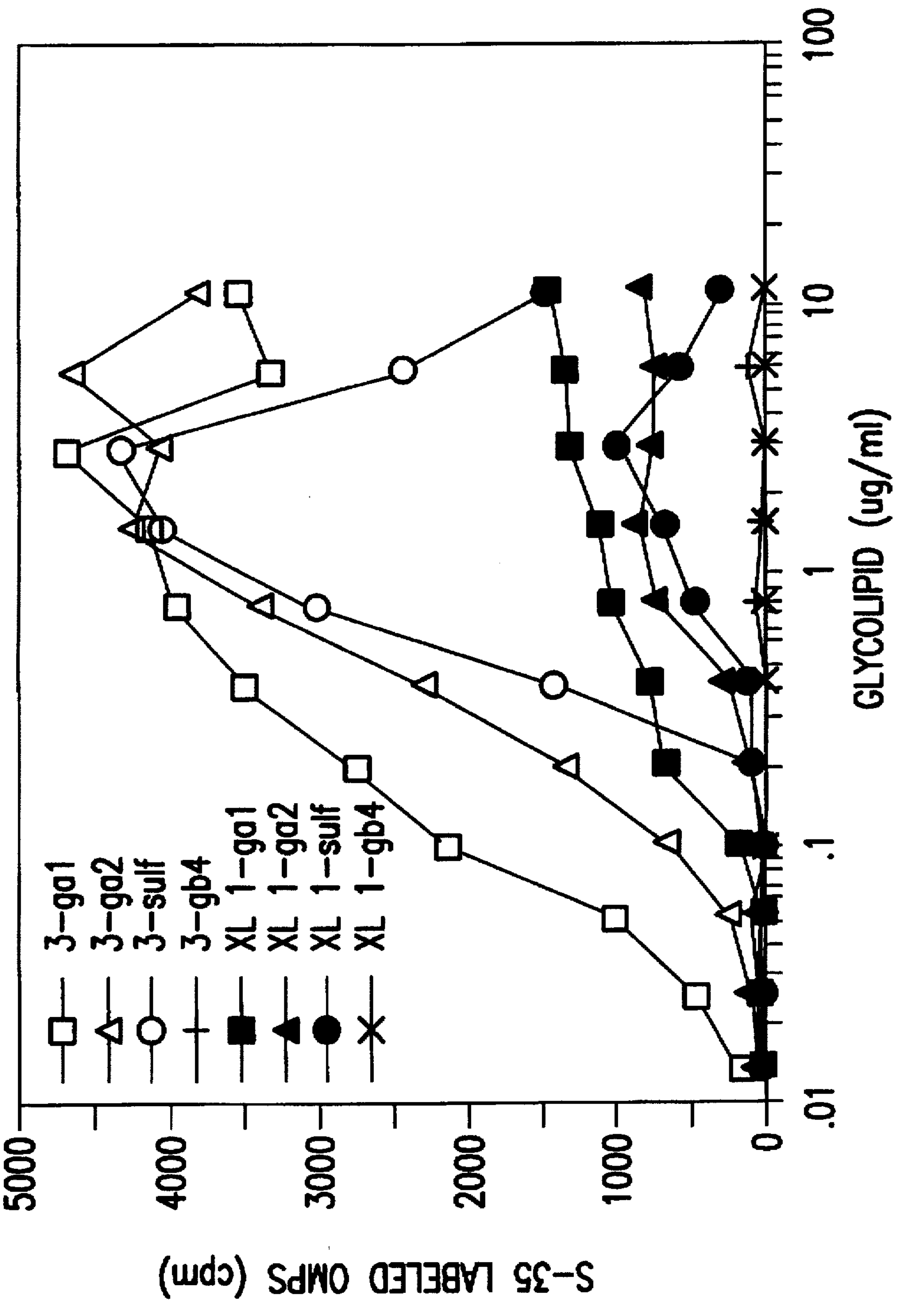
FIG. 6 shows the glycolipid binding phenotype of *Escherichia coli* that express the Hib 47 kDa protein. The ability of membranes from the *E. coli*, XL-1, or from XL-1 transformed with pMC101, designated 3, were compared using the standard binding assay. Serial dilutions were made of glycolipids with receptor activity: asialo-$GM_1$, asialo-$GM_2$, sulfatide, or the negative control, $Gb_4$. XL-1/pMC101 binds with high affinity to these receptors, similar to Haemophilus.

4. Cloning and sequencing of the gene that encodes the 47 kDa adhesin. Cloning methods were performed by standard procedures as described by Maniatis et al., *Molecular Cloning: A Laboratory Manual* (Cold Spring Harbor Laboratory, Cold Spring Harbor, N.Y.) (1982), incorporated herein by reference. Total DNA from *Haemophilus influenza* type b strain ATCC 9795 was isolated and partially digested with the restriction enzymes Eco R1 according to the manufacturer's recommendations (Boerhinger-Manheim). DNA fragments 4–15 kbp in length were isolated on a sucrose gradient and ligated to Eco RI-digested Lambda ZAPII arms as supplied by Stratagene, Inc. This ligation was then packaged into phage particles and used to tranfect the *Escherichia coli* host strain, XL-1 (according to Statagene protocol) to obtain phage plaques which express Haemophilus proteins. These plaques were used in an immunoblot screen with Hib 43 using a Stratagene Picoblue detection kit. Positive reacting plaques were purified and used to induce the production of a plasmid through the use of the helper phage R408 (according to Stratagene protocol). These plasmids carried the Haemophilus insert DNA which encoded the Hin47 immunoreactive protein. The restriction map for one of these plasmids, designated pMC101, is shown in FIG. 5. All plasmids which expressed the Hin47 protein contained the 10.5 kbp DNA from Hi. The location of the gene encoding this protein was determined by deletion analysis of pMC101. Deletion analysis was performed by generation of subclones of pMC101 containing various restriction fragments in the vector pSK(−) (Stratagene). These subclones are represented on FIG. 5 with an indication of whether each expresses a Hib 43 immunoreactive protein. The deletion analysis suggested that the Hin47 was encoded by a gene which was bounded by an approximate 2.4 kbase Pst 1 to BamH1 fragment. Therefore, sequence analysis of this entire region was performed using the dideoxy double stranded sequencing methods of Sanger et al., "Determination of Nucleotide Sequences in DNA," *Science*, 214: 1205–1210 (1981), with Sequenase® brand of DNA polymerase, (US Biochemicals). The results of this analysis are represented in FIGS. 7A and 7B. An open reading frame (ORF) was identified which would encode an approximate 49 kDa protein, comprising 463 amino acids, located between nucleotide 115 and 1503. Analysis of the amino acid sequence predicted by this ORF indicated that this protein contains a putative signal sequence of approximately 2.5 kDa and 25 amino acids. This could result in a mature protein of approximately 47 kDa and 438 amino acids as indicated by prior Western blot analysis. This ORF was designated hin47. The expression of the Hin47 protein was similar irrespective of the orientation of the gene with respect to the beta-galactosidase promoter contained in pSK(−), indicating this protein is expressed in *E. coli* under its own promoter. Membranes of *E. coli* clones that expressed this protein were compared with the membranes of *E. coli* that did not express this protein (FIG. 6). The binding curves for both membranes preparations demonstrate that this protein confers upon *E. coli* the ability to bind to the receptor with high affinity, like Haemophilus.

5. The Hin47 adhesin is a novel protein. A series of major integral membrane proteins has been characterized by several investigators (Gonzales et al., *Infect. Immun.*, 55: 2993–3000 (1987), incorporated herein by reference). These include P1, which is approximately 43 kDa, and P6, which is approximately 18 kDa. The Hin47 adhesin was analyzed to insure that it was not any of these previously characterized proteins. Using an *E. coli* clone that expressed P1 or P6, neither clone reacted with Hib 43, demonstrating that this antibody does not recognize either of these proteins. Additionally, since the P1 protein is similar in size to the Hin47 adhesin, we demonstrated by heat modification that the Hin47 adhesin was not P1. The *E. coli* which expressed P1 was separated by SDS-PAGE after treatment at room temperature or 100° C. P1 has previously been shown to be heat modifiable (Gonzales et al.). After treatment at 100° C., the protein migrates at about 43 kDa, while after treatment at room temperature, P1 migrates at about 32 kDa. The Hin47 protein was shown not to be heat modifiable. A comparison of the sequence of the 2.4 kbase Pst 1 to BamH1 fragment of pMC102 confirmed that hin47 has no homology with the gene that encodes P1.

6. Purification of the Hin47 adhesin. The Hin47 protein is purified to homogeneity using the monoclonal antibody Hib 43 as an immunoabsorbent according to Krivan et al., *Inf. and Immun.,* 55: 1873–1877 (1987). Briefly, antibody is coupled to cyanogen activated sepharose 4CL beads (Pharmacia) according to the manufacturer's recommendation. A 4 ml column containing about 8 mg of coupled antibody is used. The Hin47 protein is produced by XL-1/pMC101 grown to stationary phase in a 4 L culture in Luria Broth. The cells are pelleted by centrifugation (12,000×g, 15 min), resuspended in PBS, and sonicated. The sonicate is pelleted by centrifugation (12,000×g. 15 min) and the supernatant pelleted by centrifugation (1000,000×g, 1 h). The resultant membrane pellet is resuspended in 1% Sarkosyl (N-lauroylsarcosine) (Sigma Chemical) and pelleted by centrifugation (100,000×g, 1 h). The supernatant is exhaustively dialyzed against PBS, then applied to the antibody column. The column is then washed with PBS, and bound protein is eluted with 3.5M $MgCl_2$. This material is dialyzed against PBS and analyzed by separation on SDS-PAGE. The gel is stained by silver (Biorad). The Hin47 protein would appear as a single species, indicating purification to homogeneity.

7. Conservation of the Hin47 adhesin with the *Haemophilus influenza* serotype. The conservation within the *Haemophilus influenza* species and genus was analyzed using Western blotting of whole cells and Southern blotting using DNA isolated from whole cells. Table 5 contains the results obtained from this study. Seven non typable *H. influenza* strains, three serotype b strains and three clinical *H. influenza* strains that have not been typed all reacted with a monoclonal antibody (Hib 43) specific for that 47 kDa Hin47. The DNA from all these strains also hybridized with a DNA probe of the entire hin47 gene. This hybridization was found at high stingency levels (less than 5% mismatch) which confirmed that strong conservation of this gene within the *H. influenza* genus. A second measure of the close relationship between these sequences was demonstrated by PCR analysis. Primers that hybrized with the immediate 5' and 3' regions were able to amplify a DNA fragment from each strain that was identical in size to the hin47 gene from strain ATCC 9795, the strain that was used to originally clone hin47. The PCR analysis was performed using GeneAmp-PCR kit with AmpliTaq® brand Taq-polymerase (Perkin-Elmer Cetus).

EXAMPLE 5

Coupling Synthetic PRP to Protein

Using the Oligomers of Compound 14

A solution of human serum albumin (41 mg, 1.0 micromol) in phosphate buffer (0.1M, pH 8.0, 1.5 ml) was mixed with a solution of Compound 14 (40 micro-mol), then, after 1 hr., sodium cyanoborohydride (26 mg, 410 micro-mol) was added. The mixture was gently stirred at 37° C. for 4 days, then ultrafiltrated, diluted with water, and ultrafiltrated again. The retained material was lyophilized and purified by gel filtration on Bio-Gel P4. The appropriate fractions were collected and lyophilized. The degree of functionalization (as haptens/protein molecule) was estimated by a combination of Lowry protein determination and orcinol ribose determination. Generally, a value of 5–10 haptens/protein molecule was obtained.

Using Oligomers of Compound 16

A solution of Compound 16 (100 micro-mol) in a mixture of aqueous sodium hydroxide (0.5M, 6.0 ml), ethanol (4.0 ml), and acetic acid (180 microliters) was stirred while thiophosgene (30 microliters) was added. After 10 min., the mixture was partitioned between ethyl acetate and water, the aqueous phase was concentrated to half the volume and added to a solution of human serum albumin (164 mg, 4.0 micro-mol) in borate buffer (0.1M, pH 9.3, 6 ml). The pH was adjusted to 9.5 and the mixture was gently stirred overnight at room temperature, then ultrafiltrated, diluted with water, and ultrafiltrated again. The retained material was lyophilized and purified by gel filtration on Bio-Gel P4. The appropriate fractions were collected and lyophilized. The degree of functionalization (as haptens/protein molecule) was estimated by a combination of Lowry protein determination and orcinol ribose determination. Generally, a value of 10–20 haptens/protein molecule was obtained.

TABLE 1

PREPARATION OF MONOMERS FOR SOLID PHASE SYNTHESIS OF PRP FRAGMENTS

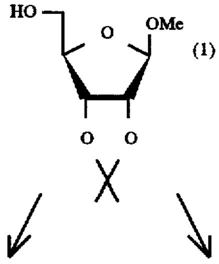

(1)

TABLE 1-continued
PREPARATION OF MONOMERS FOR SOLID PHASE SYNTHESIS OF PRP FRAGMENTS
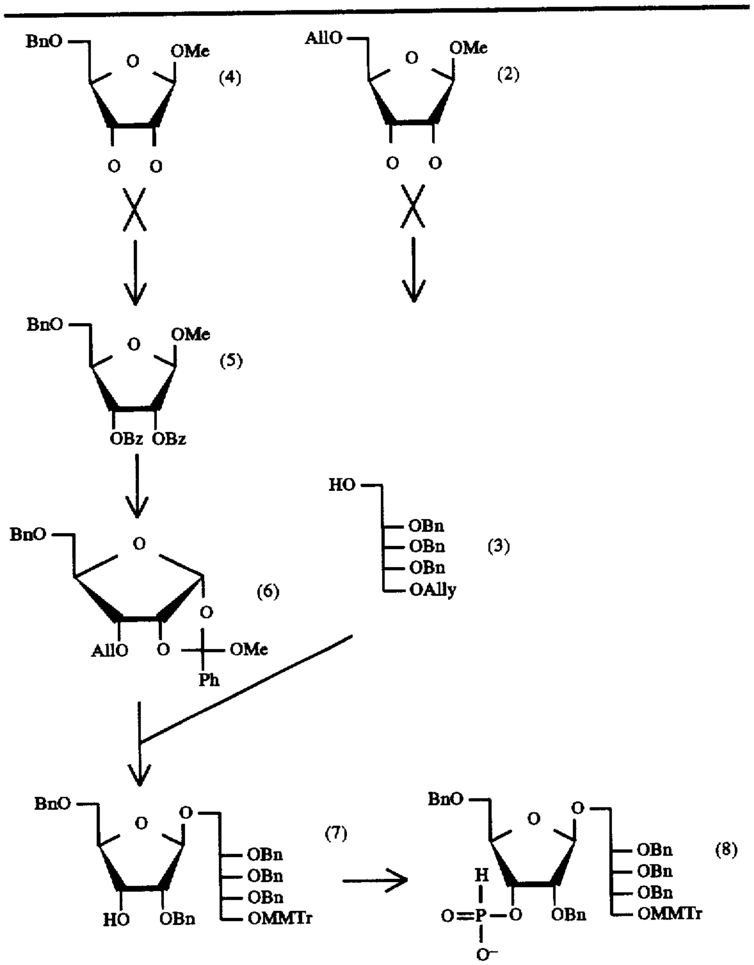
(4) (2) (5) (3) (6) (7) (8)
Monomer for chain initiation in solid phase synthesis
Monomer for chain elongation in solid phase synthesis
TABLE 2
PREPARATION OF SPACER-CONTAINING MONOMERS FOR CHAIN TERMINATION IN THE SOLID PHASE SYNTHESIS
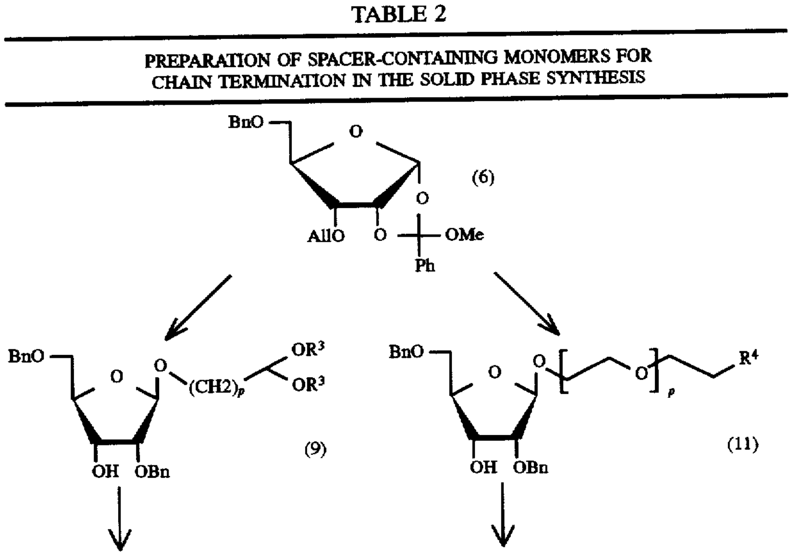
(6) (9) (11)

TABLE 2-continued
| PREPARATION OF SPACER-CONTAINING MONOMERS FOR CHAIN TERMINATION IN THE SOLID PHASE SYNTHESIS |
| --- |
| 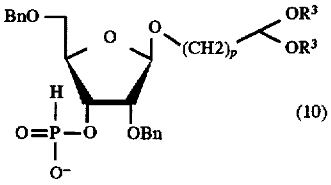 (10) 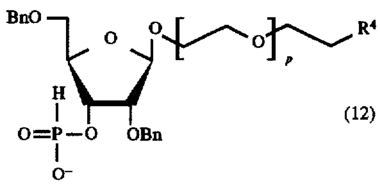 (12) |
| Monomers for chain termination in solid phase synthesis |
TABLE 3
| OLIGOMERS OBTAINED AFTER COMPLETED SOLID-PHASE SYNTHESIS |
| --- |
| 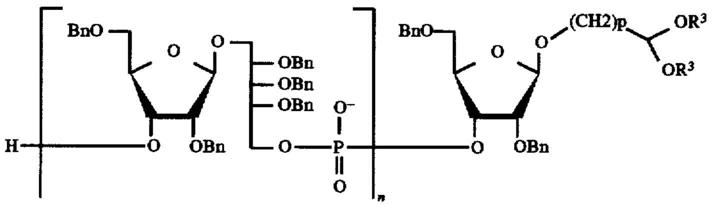 (13) |
| 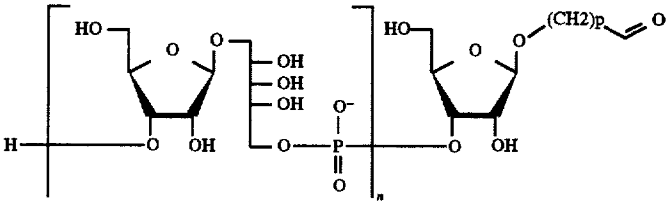 (14) |
| OR, ALTERNATIVELY: |
| 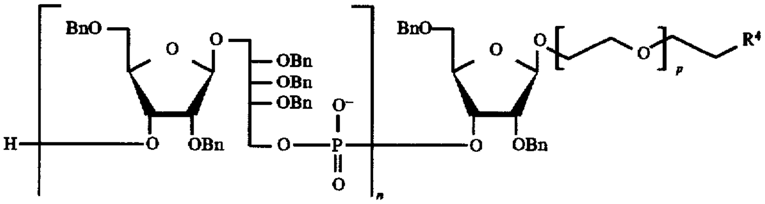 (15) |
| 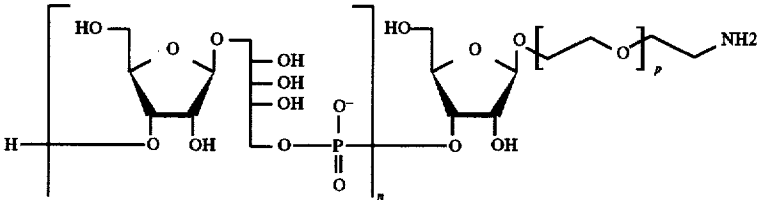 (16) |

TABLE 4

STRUCTURE OF CONJUGATES BETWEEN SYNTHETIC PRP FRAGMENT AND ADHESION PROTEIN.

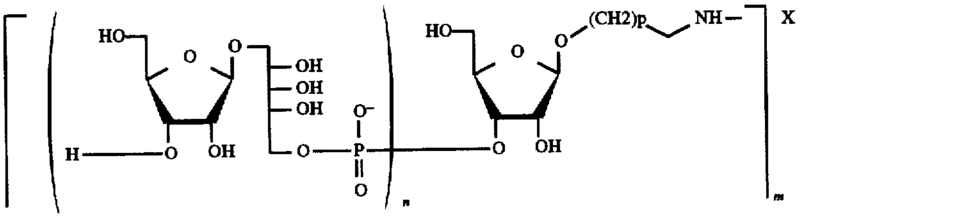

(17)

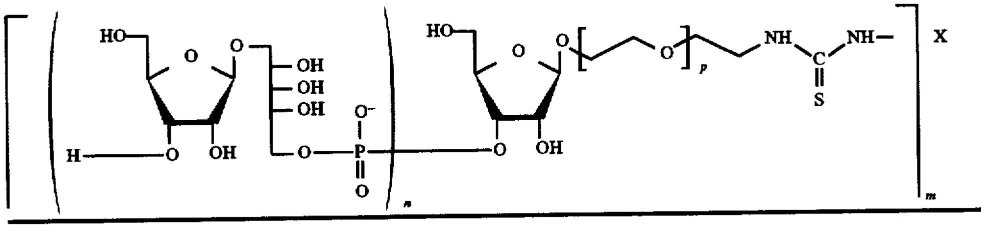

(18)

TABLE 5

Conservation of hin47

| Organism | Strain | SeroType | Immunoreactive with Hib 43 | Hybridize with hin47 |
|---|---|---|---|---|
| *Haemophilus influenza* | ATCC9795 | b | + | + |
| *H. influenza* | ATCC33533 | b | + | + |
| *H. influenza* | ATCC10200 | b | + | + |
| *H. influenza* | ATCC43095 | Non-typable | + | + |
| *H. influenza* | ATCC43041 | Non-typable | + | + |
| *H. influenza* | ATCC35902 | Non-typable | + | + |
| *H. influenza* | ATCC33391 | Non-typable | + | + |
| *H. influenza* | ATCC9333 | Non-typable | + | + |
| *H. influenza* | ATCC19418 | Non-typable | + | + |
| *H. influenza* | ATCC8149 | Non-typable | + | + |
| *H. influenza* | Clinical | NT[a] | + | + |
| *H. influenza* | Clinical | NT | + | + |
| *H. influenza* | Clinical | NT | + | + |
| *H. somnus* | bovine | NT | + | + |

We claim:

1. An isolated or substantially purified DNA comprising a contiguous nucleotide sequence selected from the group consisting of SEQ ID NO: 1, nucleotides 115 to 1503 of SEQ ID NO:1 or nucleotides 191 to 1503 of SEQ ID NO: 1.

2. The DNA of claim 1 which comprises the contiguous sequence of nucleotides 115 to 1503 of SEQ ID NO:1.

3. A method for producing an isolated DNA comprising the contiguous sequence of nucleotides 115 to 1503 of SEQ ID NO:1, which contiguous sequence encodes an *H. influenzae* protein, comprising the steps of:

screening a genomic library of *H. influenzae*, said library comprising clones which contain different sequences of *H. influenzae* genomic DNA which have been operably and recoverably inserted into a vector, by contacting the clones of said library with a monoclonal antibody to said *H. influenzae* protein or a receptor for said *H. influenzae* protein to identify a clone that binds to said antibody or said receptor;

isolating said clone; and recovering said DNA sequence from said clone.

4. An isolated or substantially purified DNA encoding a protein comprising the contiguous sequence of SEQ ID NO:2 or the contiguous sequence of amino acids 26 to 463 of SEQ ID NO:2.

5. An isolated or substantially purified DNA derived from the contiguous sequence of nucleotides 115 to 1503 of SEQ ID NO:1, which DNA sequence has one or multiple mutations and encodes a protein or polypeptide that is immunologically cross-reactive with a protein comprising the contiguous sequence of SEQ ID :2 or the contiguous sequence of amino acids 26 to 463 of SEQ ID NO:2.

6. An isolated or substantially purified DNA sequence that hybridizes under conditions of high stringency with the the contiguous sequence of nucleotides 115 to 1503 of SEQ ID NO:1 and encodes a protein or polypeptide that is immunologically cross-reactive with a protein comprising the contiguous sequence of SEQ ID NO:2 or the contiguous sequence of amino acids 26 to 463 of SEQ ID NO:2.

7. A recombinant DNA sequence comprising the DNA of claim 1 operably linked to appropriate regulatory control nucleic acid sequences which effect expression of said DNA sequence in a transformed host cell.

8. An expression vector comprising the recombinant DNA sequence of claim 7.

9. A host cell transformed with the recombinant DNA sequence of claim 7.

10. A method for producing an *H. influenzae* protein comprising the steps of:

culturing host cells transformed by a recombinant DNA comprising the contiguous sequence of nucleotides 115 to 1503 of SEQ ID NO:1 which is operably linked to appropriate regulatory control nucleic acid sequences that effect expression of said contiguous sequence in said transformed cells; and recovering the protein from said transformed cells.

11. The DNA of claim 1, which comprises the contiguous sequence of nucleotides 191 to 1503 of SEQ ID NO:1.

12. The DNA of claim 4, wherein said protein comprises the contiguous sequence of amino acids 26 to 463 of SEQ ID NO:2.

13. A method for producing an *H. influenzae* protein comprising the steps of:

culturing host cells transformed by a recombinant DNA comprising the contiguous sequence of nucleotides 191 to 1503 of SEQ ID NO:1 which is operably linked to appropriate regulatory control nucleic acid sequences that effect expression of said contiguous sequence in said transformed cells; and recovering the protein from said transformed cells.

* * * * *